(12) United States Patent
Chance et al.

(10) Patent No.: US 8,911,960 B2
(45) Date of Patent: Dec. 16, 2014

(54) METHOD FOR IDENTIFYING IDIOPATHIC PNEUMONIA PROGRESSION BY MEASURING THE LEVEL OF MANNOSE-BINDING PROTEIN C

(75) Inventors: Mark Chance, Chagrin Falls, OH (US); Kenneth Cooke, Solon, OH (US); Daniela Schlatzer, Lakwood, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 13/375,523

(22) PCT Filed: Jun. 1, 2010

(86) PCT No.: PCT/US2010/036903
§ 371 (c)(1),
(2), (4) Date: Dec. 1, 2011

(87) PCT Pub. No.: WO2010/141469
PCT Pub. Date: Dec. 9, 2010

(65) Prior Publication Data
US 2012/0077209 A1     Mar. 29, 2012

Related U.S. Application Data

(60) Provisional application No. 61/182,870, filed on Jun. 1, 2009.

(51) Int. Cl.
*G01N 33/53* (2006.01)
*G01N 33/567* (2006.01)
*G01N 33/68* (2006.01)

(52) U.S. Cl.
CPC ........ *G01N 33/6893* (2013.01); *G01N 2800/56* (2013.01); *G01N 2800/12* (2013.01); *G01N 2800/52* (2013.01); *G01N 2800/50* (2013.01); *G01N 2800/245* (2013.01)
USPC .......................................... 435/7.4; 435/7.92

(58) Field of Classification Search
CPC ....................... G01N 2800/50; G01N 2800/52
USPC .................................................. 435/7.4, 7.92
See application file for complete search history.

(56) References Cited

PUBLICATIONS

Carlson et al. (2005), J. Biol. Chem., 280(27):25541-25547.*

* cited by examiner

*Primary Examiner* — Prema Mertz
(74) *Attorney, Agent, or Firm* — Tarolli, Sundheim, Covell & Tummino LLP

(57) ABSTRACT

A method for characterizing the risk a subject will develop an autoimmune and/or alloimmune disease following tissue transplant includes obtaining a biological sample from the subject, wherein the subject has received the tissue transplant determining in the biological sample a level of at least one protein selected from Tables 1-4, comparing the measured level of the at least one protein to a control value, and characterizing a subject as at greater risk of developing an autoimmune disease and/or alloimmune disease if the level of at least one protein determined is increased or decreased compared to the control value.

3 Claims, 5 Drawing Sheets

METHOD FOR IDENTIFYING IDIOPATHIC PNEUMONIA PROGRESSION BY MEASURING THE LEVEL OF MANNOSE-BINDING PROTEIN C

RELATED APPLICATION

This application corres. to PCT/US2010/036903, filed Jun. 1, 2010, which claims priority from U.S. Provisional Application No. 61/182,870, filed Jun. 1, 2009, the subject matter which is incorporated herein by reference in their entirety.

BACKGROUND

Autoimmune diseases are generally believed to be caused by the failure of the immune system to discriminate between antigens of foreign invading organisms (non-self) and tissues native to its own body (self). When this failure to discriminate between self and non-self occurs and the immune system reacts against self antigens, an autoimmune disorder may arise. Autoimmune diseases, or diseases having an autoimmune component, include rheumatoid arthritis, multiple sclerosis, systemic lupus erythromatosis (SLE), scleroderma, diabetes, inflammatory bowel disease, psoriasis and atherosclerosis. "Alloimmune diseases" are referred to herein as disorders such as graft versus host disease and tissue transplant rejection, in which an immune response against or by foreign, transplanted tissue can lead to serious complications or be fatal. In the treatment of these disorders, it is desired to prevent the body from reacting against non-self antigens.

Allogeneic hematopoietic stem cell transplantation (SCT) is a curative therapy for malignant and non malignant conditions. Unfortunately, a number of complications can occur due to SCT treatment. One major complication is diffuse lung injury, which occurs in 25% to 55% of SCT recipients and can account for approximately 50% of all SCT related mortality. Lung injury following SCT can be infectious or noninfectious and recent advances in treatment of infectious lung injury has reduced the incidence of this complication. However, an increase in pulmonary lung injury from non-infectious etiologies has been observed and non-infectious lung injury poses a significant clinical challenge, as it is associated with significant morbidity and mortality. One type of non-infectious lung injury is idiopathic pneumonia syndrome (IPS) which is defined as widespread alveolar injury following SCT without an active lower respiratory tract infection. It is considered a clinical syndrome with the pathogeneses and diagnostic criteria of this complication remaining undefined. The incidence of IPS ranges from 5 to 25% with a median onset of approximately 14 days and an overall day 100 mortality of 80% despite aggressive treatment therapies.

IPS encompasses a spectrum of clinical presentations and is thought to result from a diversity of lung insults, including toxic effects of myeloablative conditioning, immunologic cell-mediated injury, inflammatory cytokines, and occult pulmonary infections (Fukuda et al. (2003) *Blood.* 102(8): 2777). Lung biopsies in IPS show diffuse alveolar damage, organizing or acute pneumonia, and interstitial lymphocytic inflammation. The clinical presentation and radiographic findings do not differentiate between infectious and idiopathic pneumonia. Often infection needs to be excluded by bronchoalvelor lavage (BAL) or lung biopsy. Because IPS mimics infectious pneumonia, treatment regimes for IPS include supportive care measures in conjugation with broad-spectrum anti-microbial agents with or without intravenous therapy but responses are limited and the mortality of patients who develop this disease remains high.

IPS continues to cause transplantation-related morbidity and mortality despite advances in diagnostic methods for opportunistic infections and refinements in supportive care. IPS typically occurs early after SCT, therefore advances in transplantation medicine, such as the characterization and prevention of IPS could alter the spectrum of lung injury in patients who have undergone a hematopoietic stem cell transplant.

SUMMARY OF THE INVENTION

Figure 1:
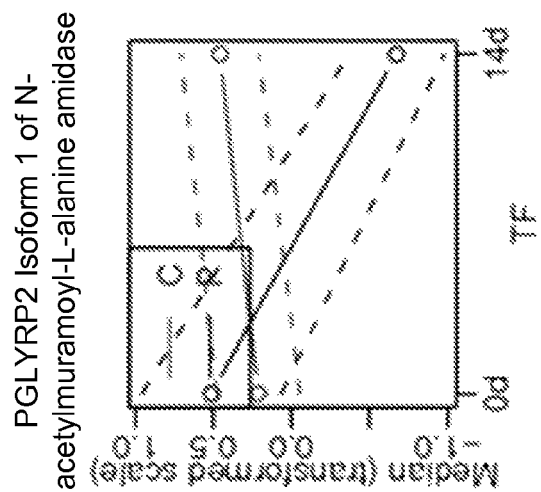
FIG. 1 illustrates interaction profiles plots of 3 selected proteins. The x-axis for each plot represents the time point and the y-axis is the intensity after data transformation in a $\log_2$ scale as described in the "Experimental Procedures" section. The solid line represents the median intensity value for peptide (s) and the dotted line is their estimated 95% confidence interval for the median difference. The values for IPS progressors subjects is indicated with a (P) and the values for control subjects is indicated with a (C). Ranking was done by minimum rank of peptides. IPI0032311: LBP Lipopolysaccharide-binding protein; IPI00020986: LUM Lumican; IPI00163207: PGLYRP2 Isoform 1 of N-acetyl-muramoyl-L-alanine amidase.
Figure 1:
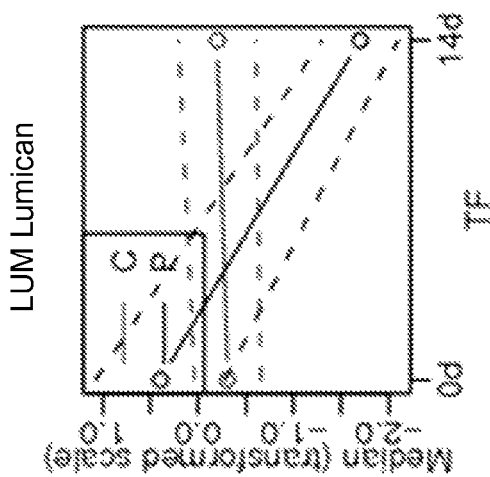
Figure 1:
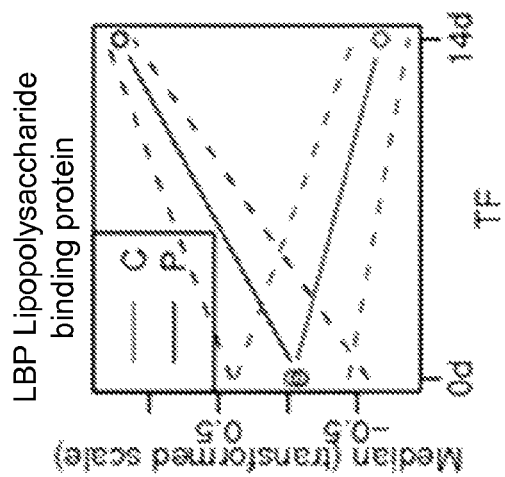

The present invention relates to the identification and measurement of proteins whose abundance levels in a biological sample from a subject can be used to characterize the risk a subject will develop and/or the progression of an autoimmune disease and/or alloimmune disease, such as Idiopathic Pneumonia Syndrome (IPS), following tissue transplant. Compared to existing methods of characterizing autoimmune disease and/or alloimmune disease following tissue transplant, the protein expression profiles disclosed herein constitute a more robust signature of autoimmune disease and/or alloimmune disease, and provide a more reliable basis for the characterization of a subject's disease as well as the selection of appropriate therapeutic regimens.

In general, the invention involves the use of expression profiles of the marker proteins listed in Tables 1, 2, 3 and 4 for characterizing the risk a subject will develop an autoimmune disease and/or alloimmune disease following tissue transplant.

TABLE 1

Protein Description

A1BG Alpha-1B-glycoprotein
A2M Alpha-2-macroglobulin
AFM Afamin
AGT Angiotensinogen
AHSG Alpha-2-HS-glycoprotein
ALDOB Fructose-bisphosphate aldolase B
AMBP AMBP protein
APCS Serum amyloid P-component
APOA1 Apolipoprotein A-I
APOA2 Apolipoprotein A-II
APOA4 Apolipoprotein A-IV
APOA4 apolipoprotein A-IV precursor
APOB Apolipoprotein B-100
APOC3 Apolipoprotein C-III
APOD Apolipoprotein D
APOE Apolipoprotein E
APOF apolipoprotein F precursor
APOH Beta-2-glycoprotein 1
APOL1 Isoform 2 of Apolipoprotein-II
APOM Apolipoprotein M
ATRN Isoform 3 of Attractin
AZGP1 alpha-2-glycoprotein 1, zinc
BTD biotinidase precursor
C14orf39 Protein SIX60S1
C1QB complement component 1, q subcomponent, Bchain precursor
C1QC Complement C1q subcomponent subunit C
C1R Complement C1r subcomponent
C1RL Complement C1r subcomponent-like protein
C3 Complement C3 (Fragment)
C4A Complement component 4A
C4B complement component 4B preproprotein
C4BPA C4b-binding protein alpha chain
C4BPB Isoform 2 of C4b-binding protein beta chain
C5 Complement C5
C7 Complement component C7
C8A Complement component C8 alpha chain
C8B Complement component C8 beta chain
C8G Complement component C8 gamma chain
C9 Complement component C9
CFB Isoform 1 of Complement factor B (Fragment)
CFH Isoform 1 of Complement factor H
CFHR2 Isoform Short of Complement factor H-related protein 2
CFI Complement factor I
CLEC3B Putative uncharacterized protein DKFZp686HI7246
CP Ceruloplasmin
CPB2 Isoform 1 of Carboxypeptidase B2
CPN1 Carboxypeptidase N catalytic chain
CRP Isoform 1 of C-reactive protein
F2 Prothrombin (Fragment)
FCN3 Isoform 1 of Ficolin-3
FGA Isoform 2 of Fibrinogen alpha chain
GC vitamin D-binding protein precursor
GMPR2 GMPR2 protein
GPX3 Glutathione peroxidase 3
GSN Isoform 1 of Gelsolin
HBB Hemoglobin subunit beta
HPX Hemopexin
HRG Histidine-rich glycoprotein
IGFALS Insulin-like growth factor-binding protein complex acid labile chain
ITIH1 Inter-alpha-trypsin inhibitor heavy chain HI
ITIH2 Inter-alpha-trypsin inhibitor heavy chain HZ
ITIH3 Isoform 1 of Inter-alpha-trypsin inhibitor heavy chain H3
KNG1 Isoform LMW of Kininogen-1

TABLE 1-continued

Protein Description

KRT1 Keratin, type II cytoskeletal 1
LBP lipopolysaccharide-binding protein
LOC653879 similar to complement component 3
LRG1 Leucine-rich alpha-2-glycoprotein
LUM Lumican
MBL2 Mannose-binding protein C
COMPLEMENT COMPONENT C6 PRECURSOR
Carboxypeptidase N subunit
C1S UNCHARACTERIZED PROTEIN ClS
F12, COAGULATION FACTOR XII
KLKB1, PLASMA KALLIKREIN PRECURSOR
ORM1 Alpha-1-acid glycoprotein 1
ORM2 Alpha-1-acid glycoprotein 2
PGLYRP2 Isoform 1 of N-acetylmuramoyl-L-alanine amidase
PLG Plasminogen
PON1 Serum paraoxonase/arylesterase 1
PON3 Serum paraoxonase/lactonase 3
POS1 Vitamin K-dependent protein S
RBP4 Retinol binding protein 4, plasma
S100A9 Protein Sl00-A9
SAA1; SAA2 Serum amyloid A protein
SAA1; SAA2 serum amyloid A2 isoform a
SAA4 Serum amyloid A-4 protein
SERPINA1 isoform 1 of Alpha-1-antitrypsin
SERPINA3 Isoform 1 of Alpha-1-antichymotrypsin
SERPINA4 Kallistatin
SERPINA6 Corticosteroid-binding globulin
SERPINA7 Thyroxine-binding globulin
SERPIND1 Serpin peptidase inhibitor, clade D (Heparin cofactor), member 1
SERPINF1 Pigment epithelium-derived factor
SERPINF2 SERPINF2 protein
SERPING1 Plasma protease C1 inhibitor
SHBG Isoform 1 of Sex hormone-binding globulin
SLC26A6 Anchor protein
SLC26A6 Long-chain fatty acid transport protein 6
TCP11L1 cDNA FU11386 fis, clone HEMBA1000523, weakly similar to TESTIS- SPECIFIC PROTEIN PBS13
TTR Transthyretin
UBTF Isoform UBF2 of Nucleolar transcription factor 1
VTN Vitronectin

TABLE 2

Protein Description

A1BG Alpha-1B-glycoprotein
AFM Afamin
AGT Angiotensinogen
AHSG Alpha-2-HS-glycoprotein
ALDOB Fructose-bisphosphate aldolase B
AMBP AMBP protein
APCS Serum amyloid P-component
APOA1 Apolipoprotein A-I
APOA2 Apolipoprotein A-II
APOA4 Apolipoprotein A-IV
APOB Apolipoprotein B-100
APOD Apolipoprotein D
APOE Apolipoprotein E
APOH Beta-2-glycoprotein 1
APOM Apolipoprotein M
ATRN Isoform 3 of Attractin
AZGP1 zinc alpha-2-glycoprotein 1

TABLE 2-continued

Protein Description

C14orf39 Protein SIX6OS1
C1QB complement component 1, q subcomponent, B chain precursor
C1QC Complement C1q subcomponent subunit C
C1R Complement C1r subcomponent
C3 Complement C3 (Fragment)
C4A Complement component 4A
C4BPA C4b-binding protein alpha chain
C5 Complement C5
C7 Complement component C7
C8A Complement component C8 alpha chain
C9 Complement component C9
CFH Isoform 1 of Complement factor H
CFHR1 Complement factor H-related protein 1
CFHR2 Isoform Short of Complement factor H-related protein 2
CFI Complement factor I
CLEC3B Putative uncharacterized protein DKFZp686H17246
CLU clusterin isoform 1
CP Ceruloplasmin
CRP Isoform 1 of C-reactive protein
F10 Coagulation factor X
F2 Prothrombin (Fragment)
FCGBP IgGFc-binding protein
FGA Isoform 2 of Fibrinogen alpha chain
GC vitamin D-binding protein precursor
GMPR2 GMPR2 protein
GPX3 Glutathione peroxidase 3
GSN Isoform 1 of Gelsolin
HPX Hemopexin
HRG Histidine-rich glycoprotein
ITIH1 Inter-alpha-trypsin inhibitor heavy chain H1
ITIH2 Inter-alpha-trypsin inhibitor heavy chain H2
ITIH3 Isoform 1 of Inter-alpha-trypsin inhibitor heavy chain H3
KNG1 Isoform LMW of Kininogen-1
KRT1 Keratin, type II cytoskeletal 1
KRT10 Keratin, type I cytoskeletal 10
LBP Lipopolysaccharide-binding protein
LRG1 Leucine-rich alpha-2-glycoprotein
LUM Lumican
ORM1 Alpha-1-acid glycoprotein 1
ORM2 Alpha-1-acid glycoprotein 2
PGLYRP2 Isoform 1 of N-acetylmuramoyl-L-alanine amidase
PLG Plasminogen
PLTP 45 kDa protein
PON1 Serum paraoxonase/arylesterase 1
S100A9 Protein S100-A9
SAA1; SAA2 Serum amyloid A protein
SAA1; SAA2 Serum amyloid A2 isoform a
SAA4 Serum amyloid A-4 protein
SERPINA1 Isoform 1 of Alpha-1-antitrypsin
SERPINA3 Isoform 1 of Alpha-1-antichymotrypsin
SERPINA4 Kallistatin
SERPINA7 Thyroxine-binding globulin
SERPIND1 Serpin peptidase inhibitor, clade D Heparin cofactor member 1
SERPINF1 Pigment epithelium-derived factor
SERPINF2 SERPINF2 protein
SERPING1 Plasma protease C1 inhibitor
SHBG Isoform 1 of Sex hormone-binding globulin
SLC26A6 Anchor protein
UBTF Isoform UBF2 of Nucleolar transcription factor 1
VTN Vitronectin

TABLE 3

Protein Description

F2 Prothrombin (Fragment)
C5 Complement C5
CFH Isoform 1 of Complement factor H
ITIH3 Isoform 1 of Inter-alpha-trypsin inhibitor heavy chain H3
APOA4 Apolipoprotein A-IV
APOB Apolipoprotein B-100
FCGBP IgGFc-binding protein
FGA Isoform 2 of Fibrinogen alpha chain
KNG1 Isoform LMW of Kininogen-1
C1QC Complement C1q subcomponent subunit C
C9 Complement component C9
SERPINA7 Thyroxine-binding globulin
CP Ceruloplasmin
APCS Serum amyloid P-component
C4BPA C4b-binding protein alpha chain
F10 Coagulation factor X
CFI Complement factor I
GPX3 Glutathione peroxidase 3
SLC26A6 Anchor protein
C1R Complement C1r subcomponent
SERPING1 Plasma protease C1 inhibitor
KRT10 Keratin, type I cytoskeletal 10
AMBP AMBP protein
C1QB complement component 1, q subcomponent, B chain precursor
SAA1; SAA2 Serum amyloid A protein
SERPINF1 Isoform 1 of Alpha-1-antitrypsin
CLU clusterin isoform 1
ORM2 Alpha-1-acid glycoprotein 2
SERPINF1 Pigment epithelium-derived factor
PLTP 45 kDa protein
ALDOB Fructose-bisphosphate aldolase B
APOE Apolipoprotein E
LRG1 Leucine-rich alpha-2-glycoprotein
LBP Lipopolysaccharide-binding protein
AZGP1 zinc alpha-2-glycoprotein 1
CRHR2 Isoform Short of Complement factor H-related protein 2
GMPR2 GMPR2 protein
ORM1 Alpha-1-acid glycoprotein 1
SAA1; SAA2 serum amyloid A2 isoform a
C14orf39 Protein SIX6OS1
SERPINA3 Isoform 1 of Alpha-1-antichymotrypsin
AGT Angiotensinogen
CRP Isoform 1 of C-reactive protein
CRHR1 Complement factor H-related protein 1
KRT1 Keratin, type II cytoskeletal 1

TABLE 4

Protein Description

VTN Vitronectin
ATRN Isoform 3 of Attractin
SHBG Isoform 1 of Sex hormone-binding globulin
AHSG Alpha-2-HS-glycoprotein
APOM Apolipoprotein M
SERPINA4 Kallistatin
GSN Isoform 1 of Gelsolin
AFM Afamin
ITIH2 Inter-alpha-trypsin inhibitor heavy chain H2
CLEC3B Putative uncharacterized protein DKFZp686H17246
C8A Complement component C8 alpha chain
APOA2 Apolipoprotein A-II
HRG Histidine-rich glycoprotein
PGLYRP2 Isoform 1 of N-acetylmuramoyl- TABLE 4-continued Protein Description L-alanine amidase
ITIH1 Inter-alpha-trypsin inhibitor heavy chain H1
UBTF Isoform UBF2 of Nucleolar transcription factor 1
APOH Beta-2-glycoprotein 1
LUM Lumican
APOA1 Apolipoprotein A-I
A1BG Alpha-1B-glycoprotein
PLG Plasminogen
SAA4 Serum amyloid A-4 protein
APOD Apolipoprotein D
HPX Hemopexin
S100A9 Protein S100-A9
GC vitamin D-binding protein precursor
SERPINF2 SERPINF2 protein
PON1 Serum paraoxonase/arylesterase 1
SERPIND1 Serpin peptidase inhibitor, clade D Heparin cofactor member 1
C4A Complement component 4A
C7 Complement component C7
C3 Complement C3 (Fragment)

Therefore, in one aspect of the present invention, a method of characterizing the risk a subject will develop an autoimmune disease and/or alloimmune disease following tissue transplant is provided. The method includes the steps of: (1) obtaining a biological sample from a subject following tissue transplant; (2) determining, in the biological sample, a level of at least one protein selected from the group consisting of proteins presented in Table 1 (i.e., Alpha-1B-glycoprotein, Alpha-2-macroglobulin, Afamin, Angiotensinogen, Alpha-2-HS-glycoprotein, Fructose-biphosphate aldolase B, AMBP protein, Serum amyloid P-component, Apolipoprotein A-I, Apolipoprotein A-II, Apolipoprotein A-IV, Apolipoprotein precursor, Apolipoprotein B-100, Apolipoprotein C-III, Apolipoprotein D, Apolipoprotein E, Apolipoprotein F precursor, Beta-2-glycoprotein 1, Isoform 2 of Apolipoprotein-L1, Apolipoprotein M, Isoform 3 of Attractin, alpha-2-glycoprotein 1 (zinc binding), biotimidase precursor, Protein SIX6OS1, complement component 1 (q subcomponent, B chain precursor), Complement C1q subcomponent subunit C, Complement C1r subcomponent, Complement C1r subcomponent-like protein, Complement C3 (Fragment), Complement component 4A, Complement component 4B preprotein, C4b-binding protein alpha chain, Isoform 2 of C4b-binding protein beta chain, Complement C5, Complement component C7, Complement component C8 alpha chain, Complement component C8 beta chain, Complement component C8 gamma chain, Complement component C9, Isoform 1 of Complement factor B (fragment), Isoform 1 of Complement factor 1-1, Isoform Short of Complement factor H-related protein 2, Complement factor 1, DKFZp686H17246, Ceruloplasmin, Isoform 1 of Carboxypeptidase B2, Carboxypeptidase N catalytic chain, Isoform 1 of C-reactive protein, Prothrombin (fragment), Isoform 1 of Ficolin-3, Isoform 2 of Fibrinogen alpha chain, vitamin D-binding protein precursor, GMPR2 protein, Glutathione peroxidase 3, Isoform 1 of Gelsolin, Hemoglobin subunit beta, Hemopexin, Histidine-rich glycoprotein, Insulin-like growth factor-binding protein complex acid labile chain, Inter-alpha-trypsin inhibitor heavy chain H1, Inter-alpha-trypsin inhibitor heavy chain H2, Isoform 1 of Inter-alpha-trypsin inhibitor heavy chain H3, Isoform LMW of Kininogen-1, Type II cytoskeletal 1 Keratin, Lipopolysaccharide-binding protein, LOC653879 similar to complement component 3, Leucine-rich alpha-2-glycoprotein, Lumican, Mannose-binding protein C, Complement component C6 precursor, Carboxypeptidase N subunit, Protein C1S, Coagulation factor XII, Plasma Kallikrein Precursor, Alpha-1-acid glycoprotein 1, Alpha-1-acid glycoprotein 2, Isoform 1 of N-acetylmuramoyl-L-alanine amidase, Plasminogen, Serum paraoxonase/arylesterase 1, Serum paraoxonase/lactonase 3, Vitamin K-dependent protein S, Retinol binding protein 4 (plasma), Protein S100-A9, Serum amyloid A protein, Serum amyloid A2 isoform a, Serum amyloid A-4 protein, Isoform 1 of Alpha-1-antitrypsin, Isoform 1 of Alpha-1-antichymotrypsin, Kallistatin, Corticosteroid-binding globulin, Thyroxine-binding globulin, Serpin peptidase inhibitor (Glade D (Heparin cofactor), member 1), Pigment epithelium-derived factor, SERPINF2 protein, Plasma protease C1 inhibitor, Isoform 1 of Sex hormone-binding globulin, Anchor protein, Long-Chain fatty acid transport protein 6, TCP11L1, Transthyretin, Isoform UBF2 of Nucleolar transcription factor 1, Vitronectin, analogs and fragments thereof; (3) comparing the measured level of the at least one protein to a control value; and (4) characterizing a subject as at greater risk of developing an autoimmune disease and/or alloimmune disease if the level of at least one protein determined is increased or decreased compared to the control value.

In some aspects, the biological sample includes a sample of blood, plasma, serum, or bronchoalveolar lavage (BAL) fluid. In some aspects, the tissue transplant includes allogeneic hematopoietic stem cell transplantation.

In some aspects of the present invention, the at least one protein is selected from the group consisting of proteins presented in Table 2 (i.e., Vitronectin, Isoform 3 of Attractin, Isoform 1 of Sex hormone-binding globulin, Alpha-2-HS-glycoprotein, Apolipoprotein M, Kallistatin, Isoform 1 of Gelsolin, Afamin, Inter-alpha-trypsin inhibitor heavy chain H2, Putative uncharacterized protein DKFZp686H17246, Complement component C8 alpha chain, Apolipoprotein A-II, Histidine-rich glycoprotein, PGLYRP1, PGLYRP2 Isoform 1 of N-acetylmuramoyl-L-alanine amidase, Inter-alpha-trypsin inhibitor heavy chain H1, Isoform UBF2 of Nucleolar transcription factor 1, Beta-2-glycoprotein 1, Lumican, Apolipoprotein A-I, Alpha-1B-glycoprotein, Plasminogen, Serum amyloid A-4 protein, Apolipoprotein D, Hemopexin, Protein S100-A9, vitamin D-binding protein precursor, SERPINF2 protein, Serum paraoxonase/arylesterase 1, Serpin peptidase inhibitor Glade D (Heparin cofactor) member 1, Complement component 4A, Complement component C7, Complement C3 (Fragment), Prothrombin (Fragment), Complement C5, Isoform 1 of Complement factor H, Isoform 1 of Inter-alpha-trypsin inhibitor heavy chain H3, Apolipoprotein A-IV, Apolipoprotein B-100, IgGFc-binding protein, Isoform 2 of Fibrinogen alpha chain, Isoform LMW of Kininogen-1, Complement C1q subcomponent subunit C, Complement component C9, Thyroxine-binding globulin, Ceruloplasmin, Serum amyloid P-component, C4b-binding protein alpha chain, Coagulation factor X, Complement factor I, Glutathione peroxidase 3, Anchor protein, Complement C1r subcomponent, Plasma protease C1 inhibitor, Keratin type I cytoskeletal 10, AMBP protein, complement component 1 q subcomponent B chain precursor, Serum amyloid A protein, Isoform 1 of Alpha-1-antitrypsin, clusterin isoform 1, Alpha-1-acid glycoprotein 2, Pigment epithelium-derived factor, 45 kDa protein, Fructose-bisphosphate aldolase B, Apolipoprotein E, Leucine-rich alpha-2-glycoprotein, Lipopolysaccharide-binding protein, zinc alpha-2-glycoprotein 1, Isoform Short of Complement factor H-related protein 2, GMPR2 protein, Alpha-1-acid glycoprotein 1, serum amyloid A2 isoform a, Protein SIX6OS1, Isoform 1 of Alpha-1- antichymotrypsin, Angiotensinogen, Isoform 1 of C-reactive protein, Complement factor H-related protein 1, and Keratin type II cytoskeletal 1).

In some aspects of the present invention, the at least one protein is selected from the group consisting of proteins presented in Table 3 (i.e., Prothrombin (Fragment), Complement C5, Isoform 1 of Complement factor H, Isoform 1 of Inter-alpha-trypsin inhibitor heavy chain H3, Apolipoprotein A-IV, Apolipoprotein B-100, IgGFc-binding protein, Isoform 2 of Fibrinogen alpha chain, Isoform LMW of Kininogen-1, Complement C1q subcomponent subunit C, Complement component C9, Thyroxine-binding globulin, Ceruloplasmin, Serum amyloid P-component, C4b-binding protein alpha chain, Coagulation factor X, Complement factor I, Glutathione peroxidase 3, Anchor protein, Complement C1r subcomponent, Plasma protease C1 inhibitor, Keratin type I cytoskeletal 10, AMBP protein, complement component 1 q subcomponent B chain precursor, Serum amyloid A protein, Isoform 1 of Alpha-1-antitrypsin, clusterin isoform 1, Alpha-1-acid glycoprotein 2, Pigment epithelium-derived factor, 45 kDa protein, Fructose-bisphosphate aldolase B, Apolipoprotein E, Leucine-rich alpha-2-glycoprotein, Lipopolysaccharide-binding protein, zinc alpha-2-glycoprotein 1, Isoform Short of Complement factor H-related protein 2, PGLYRP1, GMPR2 protein, Alpha-1-acid glycoprotein 1, serum amyloid A2 isoform a, Protein SIX6OS1, Isoform 1 of Alpha-1-antichymotrypsin, Angiotensinogen, Isoform 1 of C-reactive protein, Complement factor H-related protein 1, and Keratin type II cytoskeletal 1).

In some aspects of the present invention, the at least one protein is selected from the group consisting of proteins presented in Table 4 (i.e., Vitronectin, Isoform 3 of Attractin, Isoform 1 of Sex hormone-binding globulin, Alpha-2-HS-glycoprotein, Apolipoprotein M, Kallistatin, Isoform 1 of Gelsolin, Afamin, Inter-alpha-trypsin inhibitor heavy chain H2, Putative uncharacterized protein DKFZp686H17246, Complement component C8 alpha chain, Apolipoprotein A-II, Histidine-rich glycoprotein, PGLYRP2 Isoform 1 of N-acetylmuramoyl-L-alanine amidase, Inter-alpha-trypsin inhibitor heavy chain H1, Isoform UBF2 of Nucleolar transcription factor 1, Beta-2-glycoprotein 1, Lumican, Apolipoprotein A-I, Alpha-1B-glycoprotein, Plasminogen, Serum amyloid A-4 protein, Apolipoprotein D, Hemopexin, Protein S100-A9, vitamin D-binding protein precursor, SERPINF2 protein, Serum paraoxonase/arylesterase 1, Serpin peptidase inhibitor Glade D (Heparin cofactor) member 1, Complement component 4A, Complement component C7, and Complement C3 (Fragment)).

In some aspects of the present invention, the at least one protein is selected from the group consisting of LPS binding protein, Mannose-binding protein-C, PGLYRP2, atrractin, and lumican.

In some aspects of the present invention, the method can further include generating an expression profile based on the determined level of at least two proteins, comparing the expression profile to a control expression profile, and characterizing the subject as having greater risk of developing GVHD if the expression profile compared to the control expression profile is substantially different. In some aspects an increase or decrease of at least 5%, or at least 20%, in determined level of the at least one protein compared to the control value characterizes the subject at greater risk of developing GVHD. In some aspects, the GVHD includes idiopathic pneumonia syndrome (IPS). In some aspects, the IPS is a subtype of IPS syndrome that is responsive to treatment by a TNF-α inhibitor.

In yet another aspect of the present invention, a method of characterizing the progression of IPS in a subject following allogeneic hematopoietic stem cell transplantation is provided. The method includes the steps of (1) obtaining a biological sample from a subject, wherein the subject has received the allogeneic hematopoietic stem cell transplantation; (2) determining, in the biological sample, the level of one or more of proteins selected from the group consisting of the proteins presented in Tables 1, 2, 3, 4, and analogs and fragments thereof; (3) comparing the measured level of the at least one protein to a control value; and (4) characterizing the IPS as progressing if the level of at least one protein determined is increased or decreased compared to the control value.

In certain aspects of the present invention, the at least one protein is selected from the group consisting of LPS binding protein, Mannose-binding protein-C, PGLYRP2, attractin and lumican. In some aspects, the biological sample includes a sample of blood, plasma, serum, or bronchoalveolar lavage (BAL) fluid.

In some aspects of the present invention, the method can further include generating an expression profile based on the determined level of at least two proteins, comparing the expression profile to a control expression profile, and characterizing the IPS in a subject as progressing if the expression profile compared to the control expression profile is substantially different. In some aspects an increase or decrease of at least 5%, or at least 20%, in determined level of the at least one protein compared to the control value characterizes the IPS in the subject as progressing. In some aspects, the IPS is a subtype of idiopathic pneumonia syndrome that is responsive to treatment by a TNF-α inhibitor.

In still another aspect, the present invention provides a method for characterizing the efficacy of a TNF-α inhibitor in treating an autoimmune disease and/or alloimmune disease in a subject following tissue transplant. The method includes the steps of: (1) obtaining a biological sample from a subject, wherein the subject has received the a tissue transplant; (2) determining, in the biological sample, a level of one or more of proteins selected from the group consisting of the proteins presented in Tables 1, 2, 3, 4, and analogs and fragments thereof; (3) comparing the measured level of the at least one protein to a control value; and (4) characterizing the TNF-α inhibitor as being more effective in treating the autoimmune disease and/or alloimmune disease when administered to the subject if the level of at least one protein determined is increased or decreased compared to the control value.

In certain aspects of the present invention, the at least one protein is selected from the group consisting of LPS binding protein, Mannose-binding protein-C, PGLYRP2, attractin and lumican. In some aspects, the biological sample includes a sample of blood, plasma, serum, or bronchoalveolar lavage (BAL) fluid.

In some aspects of the present invention, the autoimmune disease and/or alloimmune disease is graft versus host disease (GVHD). In other aspects, the GVHD is IPS. In still other aspects, the IPS is a subtype of IPS syndrome that is responsive to treatment by a TNF-α inhibitor.

In a further aspect, the method can include generating an expression profile based on the determined level of at least two proteins and comparing the expression profile to a control expression profile, wherein a substantial difference in the expression profile compared to the control expression profile characterizes the TNF-α inhibitor as being more effective in treating IPS when administered to the subject. In some aspects an increase or decrease of at least 5%, or at least 20%, in determined level of the at least one protein compared to the control value characterizes the TNF-α inhibitor as being more effective in treating IPS when administered to the subject.

In still yet another aspect of the invention, a method of treating a subject having or at elevated risk of idiopathic pneumonia syndrome (IPS) following allogeneic hematopoietic stem cell transplantation is provided. The method includes the steps of: (1) obtaining a biological sample from a subject, wherein the subject has received the allogeneic hematopoietic stem cell transplantation; (2) determining, in the biological sample, a level of one or more of proteins selected from the group consisting of the proteins presented in Tables 1, 2, 3, 4, and analogs and fragments thereof; (3) comparing the measured level of the at least one protein to a control value; and (4) administering a TNF-α inhibitor to the subject to treat IPS if the level of at least one protein determined is increased or decreased compared to the control value.

In certain aspects of the present invention, the at least one protein is selected from the group consisting of LPS binding protein, Mannose-binding protein-C, PGLYRP2, attractin, and lumican. In some aspects, the biological sample includes a sample of blood, plasma, serum, or bronchoalveolar lavage (BAL) fluid.

In some aspects of the present invention, the method can further include generating an expression profile based on the determined level of at least two proteins and comparing the expression profile to a control expression profile, and administering a TNF-α inhibitor to the subject to treat IPS if there is a substantial difference in the expression profile compared to the control expression profile. In some aspects, a subject is administered a TNF-α inhibitor if the determined level of the at least one protein compared to the control increases or decreases at least 5%, or at least 20%. In some aspects, the TNF-α inhibitor includes etanercept.

DETAILED DESCRIPTION

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

The term "subject" and "individual" are used herein interchangeably. They refer to a human or another mammal that can be afflicted with an autoimmune disease or alloimmune disease, such as idiopathic pneumonia syndrome, but may or may not have the disease. In many embodiments, the subject is a human being.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

The term "biological sample" is used herein in its broadest sense. A biological sample may be obtained from a subject (e.g., a human) or from components (e.g., tissues) of a subject. The sample may be of any biological tissue or fluid with which the proteins described herein may be assayed. Frequently, the sample will be a "clinical sample", i.e., a sample derived from a patient. Such samples include, but are not limited to, bodily fluids, which may or may not contain cells, e.g., blood, blood plasma, serum, bronchoalveolar lavage (BAL) fluid, tissue or fine needle biopsy samples; and archival samples with known diagnosis, treatment and/or outcome history. Biological samples may also include sections of tissues such as frozen sections taken from histological purposes. The term biological sample also encompasses any material derived by processing the biological sample. Derived materials include, but are not limited to, cells (or their progeny) isolated from the sample, proteins or nucleic acid molecules extracted from the sample. Processing of the biological sample may involve one or more of, filtration, distillation, extraction, concentration, inactivation of interfering components, addition of reagents, and the like.

The terms "normal" and "healthy" are used herein interchangeably. In the present context, they can refer to an individual or group of individuals who have not shown any symptoms of an autoimmune disease and/or alloimmune disease following a tissue transplant, and have not been diagnosed with an autoimmune disease and/or an alloimmune disease, such as idiopathic pneumonia syndrome (IPS). In certain embodiments, normal individuals have similar sex, age, body mass index as compared with the individual from which the sample to be tested was obtained. The term "normal" is also used herein to qualify a sample isolated from an individual who has not had a tissue transplant.

In the context of the present invention, the term "control sample" refers to one or more biological samples isolated from an individual or group of individuals that are normal (i.e., healthy). A control sample can also refer to a biological sample isolated from a patient or group of patients prior to tissue transplantation (e.g., a stem cell transplantation). The term "control sample" (or "control") can also refer to the compilation of data derived from samples of one or more individuals classified as normal, or one or more individuals diagnosed with IPS, one or more individuals likely to respond well to TNF-α inhibitor treatment, or one or more individuals having undergone treatment for IPS.

As used herein, the term "differentially expressed protein" refers to a protein or polypeptide whose abundance level in a biological sample is different (e.g., increased or decreased) in a subject (or a population of subjects) afflicted with a GVHD, such as IPS, relative to a control value. The term also encompasses a protein whose level is different in subject afflicted with different subtypes of the disease (e.g., those likely to be responsive to treatment by a TNF-α inhibitor). Differential expression includes quantitative, as well as qualitative, differences in the temporal or cellular expression pattern of the biomarker. As described in greater details below, a differentially expressed protein, alone or in combination with other differentially expressed proteins, is useful in a variety of different applications in subject and disease characterization, therapeutic, drug development and related areas. The expression patterns of the differentially expressed proteins disclosed herein can be described as a fingerprint or a signature of an IPS, IPS subtype and IPS progression. They can be used as a point of reference to compare and characterize unknown samples and samples for which further information is sought.

The term "decreased level" as used herein, refers to a decrease in the abundance level of one or more of the proteins described herein of at least 5% or more. For example, 5%, 10%, 20%, 30%, 40%, or 50%, 60%, 70%, 80%, 90% or more, or a decrease of greater than 1-fold, 2-fold, 3-fold, 4-fold, 5-fold, 10-fold, 50-fold, 100-fold or more as measured by one or more methods described herein. The term "increased level" as used herein, refers to an increase in the abundance one or more of the proteins described herein of at least 5% or more. For example, 5%, 10%, 20%, 30%, 40%, or 50%, 60%, 70%, 80%, 90% or more, or an increase of greater than 1-fold, 2-fold, 3-fold, 4-fold, 5-fold, 10-fold, 50-fold, 100-fold or more as measured by one or more methods, such as a method described herein.

The terms "protein", "polypeptide", and "peptide" are used herein interchangeably, and refer to amino acid sequences of a variety of lengths, either in their neutral (uncharged) forms or as salts, and either unmodified or modified by glycosylation, side chain oxidation, or phosphorylation. In certain embodiments, the amino acid sequence is the full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversion of the chains, such as oxidation of sulfhydryl groups. Thus, the term "protein" (or its equivalent terms) is intended to include the amino acid sequence of the full-length native protein, subject to those modifications that do not change its specific properties. In particular, the term "protein" encompasses protein isoforms, i.e., variants that are encoded by the same gene, but that differ in their pI or MW, or both. Such isoforms can differ in their amino acid sequence (e.g., as a result of alternative splicing or limited proteolysis), or in the alternative, may arise from differential post-translational modification (e.g., glycosylation, acylation, phosphorylation). In certain embodiments, proteins refer to those proteins whose expression profile was found to characterize an autoimmune disorder, such as IPS, and/or the likelihood or risk of a subject having a GVHD, such as IPS, or a sub-type of IPS that is responsive to treatment by a TNF-α inhibitor.

The term "protein analog", as used herein, refers to a protein that possesses a similar or identical function as the full-length native protein but need not necessarily comprise an amino acid sequence that is similar or identical to the amino acid sequence of the protein, or possesses a structure that is similar or identical to that of the protein. Preferably, in the context of the present invention, a protein analog has an amino acid sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the amino acid sequence of the full-length native protein.

The term "protein fragment", as used herein, refers to a protein comprising an amino acid sequence of at least 4 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a second protein. The fragment of a marker protein may or may not possess a functional activity of the full-length native protein.

The terms "labeled", "labeled with a detectable agent" and "labeled with a detectable moiety" are used herein interchangeably. These terms are used to specify that an entity (e.g., a probe) can be visualized, for example, following binding to another entity (e.g., a polynucleotide or protein). Preferably, the detectable agent or moiety is selected such that it generates a signal which can be measured and whose intensity is related to the amount of bound entity. In array-based methods, the detectable agent or moiety is also preferably selected such that it generates a localized signal, thereby allowing spatial resolution of the signal from each spot on the array. Methods for labeling proteins are well-known in the art. Labeled proteins can be prepared by incorporation of or conjugation to a label, that is directly or indirectly detectable by spectroscopic, photochemical, biochemical, immunochemical, electrical, optical, or chemical means. Suitable detectable agents include, but are not limited to, various ligands, radionuclides, fluorescent dyes, chemiluminescent agents, microparticles, enzymes, calorimetric labels, magnetic labels, and haptens. Detectable moieties can also be biological molecules such as molecular beacons and aptamer beacons.

The term "IPS expression profile map" refers to a presentation of expression levels of a set of proteins in a particular status of IPS (e.g., low risk of subject developing disease, high risk of subject developing disease, IPS progression, and/or IPS subtype likely to respond positively to TNF-α inhibitor treatment). The map may be presented as a graphical representation (e.g., on paper or a computer screen), a physical representation (e.g., a gel or array) or a digital representation stored in a computer-readable medium. Each map corresponds to a particular status of the disease (e.g., low risk of subject developing disease, high risk of subject developing disease, IPS progression, and/or IPS subtype likely to respond positively to TNF-α inhibitor treatment) or to a sample taken from the patient previously, and thus provides a template for comparison to a patient sample. In certain embodiments, maps are generated from a plurality of samples obtained from a significant number of control subjects). Maps may be established for individuals with matched age, sex and body mass index.

As used herein, the term "IPS subtype that is responsive to treatment by a TNF-α inhibitor" refers to an IPS subtype susceptible to treatment through the administration of a TNF-α inhibitor. In the context of the present invention, "responsive to treatment by a TNF-α inhibitor" may include, for example: modulation of the level of at least one of the proteins described herein; and/or to delay or prevent the onset of IPS; and/or to slow down or stop the progression, aggravation, or deterioration of the symptoms of IPS; and/or to bring about amelioration of the symptoms of IPS, and/or to cure IPS.

The term "mass spectrometry" or "MS" as used herein refer to methods of filtering, detecting, and measuring ions based on their mass-to-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z").

As used herein, the term "ionization" refers to the process of generating an analyte ion having a net electrical charge equal to one or more electron units. Negative ions are those having a net negative charge of one or more electron units, while positive ions are those having a net positive charge of one or more electron units.

The present invention relates to the identification and use of proteins as systemic non-invasive (e.g., plasma) markers to characterize the risk a subject will develop an autoimmune disease and/or alloimmune disease, such as graft versus host disease, after a tissue transplant. The present invention also relates to improved methods and strategies for the characterization of idiopathic pneumonia (IPS), and sub-typing of IPS. The invention also relates to therapeutic treatments for IPS as well as methods of drug discovery.

The present invention is based in part on the discovery that the abundance levels of specific proteins are significantly modulated in subjects with IPS progression after receiving a tissue transplant compared to control values. It has also been found that changes in the abundance of proteins responsible for regulation of the immune response, such as LPS binding protein, Mannose-binding protein-C, PGLYRP2 protein, attractin, and lumican are significant predictors of the risk a subject will develop a GVHD, such as IPS, following tissue transplant.

The present invention provides the identity of a set of proteins indicative of IPS identified using high-throughput proteomics technology. The protein markers indicative of IPS are listed in Tables 1, 2, 3 and 4. The inventors analyzed samples of blood plasma obtained from subjects who had received a tissue transplant and who were afflicted with IPS. The inventors then compared the protein expression level from these samples to samples obtained from subjects who had received a tissue transplant but were not afflicted by IPS. It was found that the proteins listed in Tables 1, 2, 3 and 4 can be used to discriminate between tissue transplant recipients likely to develop IPS and tissue transplant recipients who are not likely to develop IPS as early as day 0 post-tissue transplant even when signs of non-infectious diffuse lung injury related to IPS would not be visible.

It was also found that the proteins listed in Tables 1, 2, 3 and 4 can be used to discriminate between an IPS subtype which is responsive to treatment through the administration of a TNF-α inhibitor and IPS that is not likely to be responsive to TNF-α inhibitor treatment. The present invention describes specific proteins and assays in biological samples to detect the identified proteins.

Extensive research in animal models supports non-infectious lung injury, e.g., idiopathic pneumonia syndrome (IPS), as an immune mediated attack that includes elements of the adaptive and innate immune system. Without being bound by theory, it is thought that graft-versus-host disease (GVHD) and/or autoimmune phenomena are responsible for the development of IPS in subjects who have received a tissue transplant. The early post-tissue transplant phase is characterized by the presence of inflammatory cytokines whose net effect is to promote lymphocyte influx into lungs with minimal fibrosis that leads to an acute form of graft-versus-host reaction-mediated pulmonary tissue damage. Gradual changes over time in leukocyte influx and activation lead to dysregulated wound repair mechanisms resulting from the shift in the balance of cytokines that promote fibrosis. Thus, it is believed that cytokine-modulated immunological mechanisms, which occur during the acute and chronic phases after tissue transplantation lead to the development of the progressive, inflammatory, and fibrotic lung disease typical of idiopathic pneumonia syndrome.

As discussed above, GVHD may be responsible for the development of IPS in subjects who have received a tissue transplant. Thus, it is also contemplated by the present invention that changes in the abundance of the identified protein markers described herein characterize the subject's risk of developing a GVHD.

Therefore, one aspect of the present invention provides a method for characterizing the risk a subject will develop an autoimmune disease and/or alloimmune disease, such as GVHD, following tissue transplant. The method includes the steps of: (1) obtaining a biological sample from a subject, wherein the subject has received a tissue transplant; (2) determining, in the biological sample, a level of at least one protein selected from the group consisting of proteins presented in Tables 1, 2, 3, 4, analogs and fragments thereof; (3) comparing the measured level of the at least one protein to a control value; and (4) characterizing a subject as at greater risk of developing an autoimmune disease and/or an alloimmune disease, such as GVHD, if the level of at least one protein determined is increased or decreased compared to the control value.

An autoimmune disease and/or alloimmune disease in a subject can include but is not limited to idiopathic pneumonia syndrome, rheumatoid arthritis, refractory arthritis, Crohn's disease, psoriasis, psoriatic arthritis, ankylosing sondylitits, idiopathic inflammatory bowel disease, and juvenile idiopathic arthritis.

The control value can be determined from samples obtained from a healthy individual (or a group of healthy individuals), from an individual (or group of individuals) prior to tissue transplantation, from an individual (or group of individuals) afflicted with IPS, and/or from an individual (or group of individuals) afflicted with a specific subtype of the disease (e.g., a subtype of IPS responsive to TNF-αt inhibitor treatment). In some aspects, the control expression levels of the biomarkers of interest are preferably determined from a significant number of individuals, and an average or mean is obtained.

A tissue transplant, as contemplated by the present invention is used in its broadest meaning and refers to both autologous and allogeneic tissue transplants. In some aspects of the invention, a tissue transplant for use in the present methods may include, but is not limited to transplantation of bone marrow, blood, stem cells, brain, heart, lung, cornea, fetal tissue, kidney liver, skin and islets of Langerhans. In certain embodiments, the tissue transplant includes a hematopoietic stem cell transplant.

The methods of the present invention may be further used to characterize the risk a subject will develop IPS following a hematopoietic stem cell transplant. Therefore, in another aspect of the present invention, a method of characterizing the risk a subject will develop IPS following a hematopoietic stem cell transplant is provided. The method includes the steps of: (1) obtaining a biological sample from a subject, wherein the subject has received the allogeneic hematopoietic stem cell transplantation; (2) determining, in the biological sample, the level of one or more of proteins selected from the group consisting of the proteins presented in Tables 1, 2, 3, 4, and analogs and fragments thereof; (3) comparing the measured level of the at least one protein to a control value; and (4) characterizing a subject as at greater risk of developing IPS if the level of at least one protein determined is increased or decreased compared to the control value.

As shown in the Examples below, it has been discovered in subject's diagnosed with IPS, that the abundance level of certain proteins will continue to increase or decrease over time compared to a control value. Therefore, it is further contemplated by the present invention that an increase or decrease in the abundance level of proteins found to be significantly modulated in subjects with IPS progression can be determined in order to characterize the progression of IPS in a subject. For example, a sample taken from a subject following a stem cell transplant which includes a significantly increased level of at least one protein compared to a sample taken from the subject previously, can characterize the IPS in the subject as progressing. On the other hand, a sample taken from a subject following a stem cell transplant may include a significantly decreased level of at least one protein compared to a sample taken from the subject previously. In this case, the decreased abundance level may characterize the IPS in the subject as not progressing, and even regressing.

Thus in accordance with another aspect of the present invention, a method of characterizing the progression of IPS in a subject is provided. The method includes the steps of (1) obtaining a biological sample from a subject, wherein the subject has received the allogeneic hematopoietic stem cell transplantation; (2) determining, in the biological sample, the level of one or more of proteins selected from the group consisting of the proteins presented in Tables 1, 2, 3, 4, and analogs and fragments thereof; (3) comparing the measured level of the at least one protein to a control value; and (4) characterizing the IPS as progressing if the level of at least one protein determined is increased or decreased compared to the control value.

In some aspects of the invention, information on abundance levels of proteins in a biological sample obtained from individuals afflicted with a GVHD, IPS or a particular subtype of the disease (e.g., IPS that is responsive to TNF-α inhibitor treatment) may be grouped to form a specific expression profile map. In one example, an IPS expression profile map results from the study of a large number of individuals with the same disease sub-type. In some embodiments, an IPS expression profile map is established using samples from individuals with matched age, sex, and body index. Each expression profile map provides a template for comparison to protein expression patterns generated from unknown biological samples. Expression profile maps may be presented as a graphical representation (e.g., on paper or a computer screen), a physical representation (e.g., a gel or array) or a digital representation stored in a computer-readable medium. In certain aspects of the invention, the level of at least one protein in the biological sample under investigation is determined and compared to at least one expression profile map for IPS, as described above.

The methods of the invention may be applied to the study of any type of biological samples allowing one or more inventive protein biomarkers to be assayed. Examples of biological samples include, but are not limited to, urine, blood, and blood products (e.g., blood plasma). In a particular aspect of the present invention, the biological sample is blood plasma obtained from the subject.

The biological samples used in the practice of the inventive methods may be fresh or frozen samples collected from a subject, or archival samples with known diagnosis, treatment and/or outcome history. Biological samples may be collected by any non-invasive means, such as, for example, by drawing blood from a subject, or using fine needle aspiration or needle biopsy. Alternatively, biological samples may be collected by an invasive method, including, for example, surgical biopsy. In certain aspects, the inventive methods are performed on the biological sample itself without or with limited processing of the sample.

In still other embodiments, the inventive methods are performed on a protein extract prepared from the biological sample. Preferably, the protein extract contains the total protein content. However, the methods may also be performed on extracts containing one or more of: membrane proteins, nuclear proteins, and cytosolic proteins. Methods of protein extraction are well known in the art (see, for example "Protein Methods", D. M. Bollag et al., 2nd Ed., 1996, Wiley-Liss; "Protein Purification Methods: A Practical ApprIPSch", E. L. Harris and S. Angal (Eds.), 1989; "Protein Purification Techniques: A Practical Approach", S. Roe, 2nd Ed., 2001, Oxford University Press; "Principles and Reactions o/Protein Extraction, Purification, and Characterization", H. Ahmed, 2005, CRC Press: Boca Raton, Fla.). Numerous different and versatile kits can be used to extract proteins from bodily fluids and tissues, and are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.). User Guides that describe in great detail the protocol to be followed are usually included in all these kits. Sensitivity, processing time and costs may be different from one kit to another. One of ordinary skill in the art can easily select the kits most appropriate for a particular situation. After the protein extract has been obtained, the protein concentration of the extract is preferably standardized to a value being the same as that of the control sample in order to allow signals of the protein markers to be quantitated. Such standardization can be made using photometric or spectrometric methods or gel electrophoresis.

The methods of the present invention generally involve the determination of the abundance levels of a plurality (i.e., one or more, e.g., at least 2, at least 3, at least 4, at least 5, at least 6, at least 7, at least 8, at least 9, at least 10 or more) of proteins in a biological sample obtained from a subject. Determination of protein levels in the practice of the inventive methods may be performed by any suitable method (see, for example, E. Harlow and A. Lane, "Antibodies: A Laboratories Manual", 1988, Cold Spring Harbor Laboratory: Cold Spring Harbor, N.Y.).

In general, protein levels are determined by contacting a biological sample isolated from a subject with binding agents for one or more of the protein markers listed in Table 1; determining, in the sample, the levels of proteins that bind to the binding agents; and comparing the levels of proteins in the sample with the levels of proteins in a control sample. As used herein, the term "binding agent" refers to an entity such as a protein or antibody that specifically binds to an inventive protein marker. An entity "specifically binds" to a protein if it reacts/interacts at a detectable level with the protein but does not react/interact detectably with peptides containing unrelated sequences or sequences of different proteins.

In certain aspects of the invention, the binding agent is a peptide component, a protein that comprises a protein sequence of a protein marker, a peptide variant thereof, or a non-peptide mimetic of such a sequence.

In other aspects, the binding agent is an antibody specific for a protein marker of the invention. Antibodies for use in the methods of the present invention include monoclonal and polyclonal antibodies, immunologically active fragments (e.g., Fab or (Fab)$_2$ fragments), antibody heavy chains, humanized antibodies, antibody light chains, and chimeric antibodies. Antibodies, including monoclonal and polyclonal antibodies, fragments and chimeras, may be prepared using methods known in the art (see, for example, R. G. Mage and E. Lamoyi, in "Monoclonal Antibody Production Techniques and Applications", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-

203; R. A. Lerner, Nature, 1982, 299: 593-596; A. C. Nairn et al., Nature, 1982, 299: 734-736; A. J. Czernik et al., Methods Enzymol. 1991, 201: 264-283; A. J. Czernik et al., Neuromethods: Regulatory Protein Modification: Techniques & Protocols, 1997, 30: 219-250; A. J. Czernik et al., Neuro-Neuroprotocols, 1995, 6: 56-61; H. Zhang et al., J. Biol. Chem. 2002, 277: 39379-39387; S. L. Morrison et al., Proc. Natl. Acad. Sci., 1984, 81: 6851-6855; M. S, Neuberger et al., Nature, 1984, 312: 604-608; S. Takeda et al., Nature, 1985, 314: 452-454). Antibodies to be used in the methods of the invention can be purified by methods well known in the art (see, for example, S. A. Minden, "Monoclonal Antibody Purification", 1996, IBC Biomedical Library Series: Southbridge, Mass.). For example, antibodies can be affinity purified by passage over a column to which a protein marker or fragment thereof is bound. The bound antibodies can then be eluted from the column using a buffer with a high salt concentration. Instead of being prepared, antibodies to be used in the methods of the present invention may be obtained from scientific or commercial sources.

In certain embodiments, the binding agent is directly or indirectly labeled with a detectable moiety. The role of a detectable agent is to facilitate the detection step of the diagnostic method by allowing visualization of the complex formed by binding of the binding agent to the protein marker (or analog or fragment thereof). Preferably, the detectable agent is selected such that it generates a signal which can be measured and whose intensity is related (preferably proportional) to the amount of protein marker present in the sample being analyzed. Methods for labeling biological molecules such as proteins and antibodies are well-known in the art (see, for example, "Affinity Techniques. Enzyme Purification. Part B", Methods in Enzymol., 1974, Vol. 34, W. B. Jakoby and M. Wilneck (Eds.), Academic Press: New York, N.Y.; and M. Wilchek and E. A. Bayer, Anal. Biochem., 1988, 171: 1-32).

Any of a wide variety of detectable agents can be used in the practice of the present invention. Suitable detectable agents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In certain aspects, the binding agents (e.g., antibodies) may be immobilized on a carrier or support (e.g., a bead, a magnetic particle, a latex particle, a microtiter plate well, a cuvette, or other reaction vessel). Examples of suitable carrier or support materials include agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinylether-maleic acid copolymer, amino acid copolymer, ethylene-maleic acid copolymer, nylon, silk, and the like. Binding agents may be indirectly immobilized using second binding agents specific for the first binding agents (e.g., mouse antibodies specific for the protein markers may be immobilized using sheep anti-mouse IgG Fc fragment specific antibody coated on the carrier or support).

Protein levels in the methods of the present invention may be determined using immunoassays. Examples of such assays are radioimmunoassays, enzyme immunoassays (e.g., ELISA), immunofluorescence immunoprecipitation, latex agglutination, hemagglutination, and histochemical tests, which are conventional methods well-known in the art. As will be appreciated by one skilled in the art, the immunoassay may be competitive or noncompetitive. Methods of detection and quantification of the signal generated by the complex formed by binding of the binding agent with the protein marker will depend on the nature of the assay and of the detectable moiety (e.g., fluorescent moiety).

Alternatively, the protein levels may be determined using mass spectrometry based methods or image (including use of labeled ligand) based methods known in the art for the detection of proteins. Other suitable methods include proteomics-based methods. Proteomics, which studies the global changes of protein expression in a sample, typically includes the following steps: (1) separation of individual proteins in a sample by electrophoresis (1-D PAGE), (2) identification of individual proteins recovered from the gel (e.g., by mass spectrometry or N-terminal sequencing), and (3) analysis of the data using bioinformatics.

In some aspects, one or more proteins can be separated by liquid chromatography (LC) and then conveniently detected and quantified by mass spectrometry (MS). Liquid chromatography removes impurities and may be used to concentrate the proteins for detection. Traditional LC relies on chemical interactions between sample components and a stationary phase such as a column packing. Laminar flow of the sample, mixed with a mobile phase, through the column is the basis for separation of the components of interest. The skilled artisan understands that separation in such columns is a partition process.

In various embodiments, one or more of the purification and/or analysis steps can be performed in an automated fashion. By careful selection of valves and connector plumbing, two or more chromatography columns can be connected as needed such that material is passed from one to the next without the need for any manual steps. In certain embodiments, the selection of valves and plumbing is controlled by a computer pre-programmed to perform the necessary steps. The chromatography system can also be connected in-line to the detector system, e.g., an MS system. Thus, an operator may place a tray of purified samples in an autosampler, and the remaining operations are performed under computer control, resulting in purification and analysis of all samples selected. In one embodiment, a diverter valve is placed in-line between the LC column and the interface with the MS. The diverter valve directs the LC effluent into a waste container until slightly prior to the time expected peak retention). This prevents the solvent front and other impurities from being passed into the MS device.

As used here, "in-line" refers to a configuration in which the LC and the ionization/injection device for the first MS quadropole are functionally connected in order that the LC effluent passes directly into the first MS device. "In-line" configurations may include a selector valve such that the effluent from two or more LC columns may be directed individually into the MS device and, optionally, to a waste container. Such a configuration is useful for a high throughput system and reduces the analysis time required for a large number of samples. High throughput systems may be designed in which an autosampler initiates LC purifications on the two or more LC columns at staggered intervals. In this way, the purified protein of interest peak is eluted from each LC column at a known interval. In certain embodiments, the purified protein peaks eluting from the two or more LC columns are directed into the MS device in rapid succession, but with sufficient temporal separation that individual measurements are not compromised. Such a high throughput system reduces the amount of "idle-time" for MS detection attributable to the LC procedure, which typically requires more time than the MS analysis.

By contrast, "off-line" refers to a configuration that requires manual intervention to transfer the LC effluent to the MS device. Typically, the LC effluent is captured by a fractionator and must be manually loaded into a MS device or into an autosampler for subsequent MS detection. Off-line configurations are useful, but less desirable because of the increased time required to process large numbers of samples.

In an aspect of the invention, the mass-to-charge ratio can be determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

"Tandem mass spectrometry" or "MS/MS" can be employed to enhance the resolution of the MS technique. In tandem mass spectrometry, a parent ion generated from a molecule of interest may be filtered in an MS instrument, and the parent ion subsequently fragmented to yield one or more daughter ions that are then analyzed (detected and/or quantified) in a second MS procedure.

Collision-induced dissociation ("CID") is often used to generate the daughter ions for further detection. In CID, parent ions gain energy through collisions with an inert gas, such as argon, and subsequently fragmented by a process referred to as "unimolecular decomposition." Sufficient energy must be deposited in the parent ion so that certain bonds within the ion can be broken due to increased vibrational energy.

By careful selection of parent ions using the first MS procedure, only ions produced by certain analytes of interest are passed to the fragmentation chamber to generate the daughter ions. Because both the parent and daughter ions are produced in a reproducible fashion under a given set of ionization/fragmentation conditions, the MS/MS technique can provide an extremely powerful analytical tool. For example, the combination of filtration/fragmentation can be used to eliminate interfering substances, and can be particularly useful in complex samples, such as biological samples.

The mass spectrometer typically provides the user with an ion scan; that is, the relative abundance of each m/z over a given range (e.g., 10 to 1200 amu). The results of an analyte assay, that is, a mass spectrum, can be related to the amount of the analyte in the original sample by numerous methods known in the art. For example, given that sampling and analysis parameters are carefully controlled, the relative abundance of a given ion can be compared to a table that converts that relative abundance to an absolute amount of the original molecule.

Alternatively, molecular standards (e.g., internal standards and external standards) can be run with the samples, and a standard curve constructed based on ions generated from those standards. Using such a standard curve, the relative abundance of a given ion can be converted into an absolute amount of the original molecule. In certain preferred embodiments, an internal standard is used to generate a standard curve for calculating the quantity of inventive protein biomarkers described herein. Numerous other methods for relating the presence or amount of an ion to the presence or amount of the original molecule are well known to those of ordinary skill in the art.

Once the levels of the biomarkers of interest have been determined for the biological sample being analyzed, they are compared to the levels in one or more control samples or to at least one expression profile map described herein. Comparison of levels according to methods of the present invention is preferably performed after the levels obtained have been corrected for both differences in the amount of sample assayed and variability in the quality of the sample used (e.g., amount of protein extracted). Correction may be carried out using different methods well-known in the art. For example, the protein concentration of a sample may be standardized using photometric or spectrometric methods or gel electrophoresis (as already mentioned above) before the sample is analyzed.

For a given set of inventive proteins, comparison of an expression pattern obtained for a biological sample against an expression profile map established as described herein may comprise a comparison of the normalized levels on a biomarker-by-biomarker basis and/or comparison of ratios of levels within the set of protein markers. In addition, the protein expression pattern obtained for the biological sample being analyzed, may be compared against each of the expression profile maps (e.g., expression profile map for low or no risk of IPS, expression profile map for high risk of IPS, expression profile map for progression of IPS, expression profile map for IPS responsive to treatment by a TNF-α inhibitor) or against an expression profile that defines delineations made based upon all the IPS expression profile maps.

In another aspect of the invention, skilled physicians may select and prescribe treatments adapted to each individual subject based on the methods described herein of characterizing the risk a subject will develop IPS and/or a specific IPS sub-type following allogeneic hematopoietic stem cell transplantation. In particular, the present invention provides physicians with a non-subjective means to characterize the risk a subject will develop IPS as early as day 0 post tissue transplant, which will allow for early treatment, when intervention is likely to have its greatest effect. Selection of an appropriate therapeutic regimen for a given patient may be made based solely on the characterization of risk (e.g., a high level of risk) provided by the inventive methods. Alternatively, the physician may also consider other clinical or pathological parameters used in existing methods to diagnose IPS and assess its advancement.

In some aspects, GVHD, and IPS diagnosed by the methods of the present invention, may be treated with a TNF-α inhibitor. Recent studies have shown that the lung fluid of patients with IPS contains higher than normal amounts of inflammatory protein that may directly damage the lung (Yanik et al. Blood (2008) 112(8):3073-3081). One such example is tumor necrosis factor-alpha (TNF-α) which may also be involved in lung injury from IPS. Tumor necrosis factor promotes the inflammatory response, which, in turn, causes many of the clinical problems associated with autoimmune diseases and/or alloimmune diseases, such as rheumatoid arthritis, ankylosing spondylitis, Crohn's disease, psoriasis and refractory asthma.

Autoimmune diseases and/or alloimmune diseases are sometimes treated by using a TNF-α inhibitor. For example, it has been shown that the TNF-α inhibitor etanercept can be used for the treatment of IPS (Yanik and Cooke (2009) Blood. 113: 2869). In general, TNF-α inhibition can be achieved with a monoclonal antibody such as infliximab or adalimumab, or with a circulating soluble receptor fusion protein such as etanercept. While most clinically useful TNF-α inhibitors are monoclonal antibodies, some are simple molecules, such as pentoxifylline and bupropion. Certolizumab pegol is a monoclonal antibody directed against tumor necrosis factor alpha. More precisely, it is a PEGylated Fab' fragment of a humanized TNF-α inhibitor monoclonal antibody.

It is further contemplated by the present invention that once a subject is characterized as having an elevated risk of idiopathic pneumonia syndrome (IPS) following allogeneic hematopoietic stem cell transplantation using the methods described above, a TNF-α inhibitor may be administered to treat the subject. In one particular example, a subject can be administered a TNF-α inhibitor when levels of at least one protein consisting of LPS binding protein, Mannose-binding protein-C, PGLYRP2, attractin and lumican are elevated prior to or post allogeneic hematopoietic stem cell transplant. In another example, a subject can be administered a TNF-α inhibitor when levels of at least one protein consisting of Mannose-binding protein-C, PGLYRP2, attractin and lumican are elevated prior to or post allogeneic hematopoietic stem cell transplant.

Therefore, in another aspect of the invention, a TNF-α inhibitor (e.g., etanercept), may be used to treat IPS in the subject who has been characterized with a sub-type of IPS that is responsive to treatment by a TNF-α inhibitor. The TNF-α inhibitor administered to the subject can include, but is not limited to, etanercept, infliximab, adalimumab, certolizumab pegol, golimumab (simponi), lenercept, semapimod (a mapK inhibitor that reduces production of TNFa), pentoxifylline, thalidomide, and benzopyranes.

In another aspect, the present invention provides a method for the treatment and/or prevention of IPS. The method includes administering to a subject an effective amount of a compound that modulates the level of at least one inventive biomarker described herein (e.g., an agent that modulates the level of the proteins listed in Table 1, 2, 3 and 4). The compound may be known in the art to act as a modulator of the level of at least one inventive biomarker.

For example, the levels of the proteins proteins LPS binding protein, Mannose-binding protein-C, PGLYRP2, attractin and lumican, which are responsible for the regulation of the immune response, were identified by the inventors as significantly modulated in the plasma of subject's having IPS compared to a control (see Example below). Thus, LPS binding protein, Mannose-binding protein-C, PGLYRP2, attractin and lumican are appropriate molecular targets for the treatment of IPS. Therefore, agents which are effective in modulating LPS binding protein, Mannose-binding protein-C, PGLYRP2, attractin and/or lumican level in a subject (e.g., an anti-LPS binding protein or an anti-lumican antibody) are contemplated by the present invention.

Subjects that can receive a treatment according to the present invention include individuals that have been diagnosed with IPS using conventional methods (e.g., radiological examination, clinical observations) as well as individuals that have been diagnosed with IPS using diagnostic methods provided herein. Suitable subjects may or may not have previously received traditional treatment for the condition.

A treatment according to the methods of the present invention may consist of a single dose or a plurality of doses over a period of time. An agent used in the present invention, or pharmaceutical composition thereof, may also be released from a depot form per treatment. The administration may be carried out in any convenient manner such as by injection (subcutaneous, intravenous, intramuscular, intraperitoneal, or the like), oral administration, topical administration, rectal administration, or sublingual administration.

Effective dosages and administration regimens can be readily determined by good medical practice and the clinical condition of the individual subject. The frequency of administration will depend on the pharmacokinetic parameters of the active ingredient(s) and the route of administration. The optimal pharmaceutical formulation can be determined depending upon the route of administration and desired dosage. Such formulations may influence the physical state, stability, rate of in vivo release, and rate of in vivo clearance of the administered compounds.

Depending on the route of administration, a suitable dose may be calculated according to body weight, body surface area, or organ size. Optimization of the appropriate dosage can readily be made by those skilled in the art in light of pharmacokinetic data observed in human clinical trials. The final dosage regimen will be determined by the attending physician, considering various factors which modify the action of drugs, e.g., the drug's specific activity, the severity of the damage and the responsiveness of the patient, the age, condition, body weight, sex and diet of the patient, the severity of any present infection, time of administration and other clinical factors.

The rapid progression to respiratory failure and the high mortality rate after IPS onset, despite advances in critical care, emphasizes the need to characterize the efficacy of a TNF-α inhibitor in treating idiopathic pneumonia syndrome (IPS) in a subject following allogeneic hematopoietic stem cell transplantation. Therefore, a method of characterizing the efficacy of a TNF-α inhibitor is contemplated by the present invention. The method includes obtaining a biological sample from the subject and determining the level of at least one protein of interest in the sample. The method further includes comparing the measured level of the at least one protein to a control value and characterizing TNF-α inhibitor as being more effective in treating IPS when administered to the subject if the level of the at least on protein determined is increased or decreased compared to a control value.

In another aspect, the present invention provides kits comprising materials useful for carrying out the methods according to the present invention. The characterization procedures described herein may be performed by diagnostic laboratories, experimental laboratories, or practitioners. The invention provides kits, which can be used in these different settings.

Materials and reagents for characterizing biological samples obtained from a subject according to the inventive methods may be assembled together in a kit. In certain aspects, an inventive kit comprises at least one reagent that specifically detects levels of one or more inventive protein markers, and instructions for using the kit according to a method of the invention. Each kit may preferably include the reagent, which renders the procedure specific. Thus, for detecting/quantifying a protein marker (or an analog or fragment thereof), the reagent that specifically detects levels of the protein may be an antibody that specifically binds to the protein marker (or analog or fragment thereof).

Depending on the procedure, the kit may further comprise one or more of, extraction buffer and/or reagents, amplification buffer and/or reagents, hybridization buffer and/or reagents, immunodetection buffer and/or reagents, labeling buffer and/or reagents, and detection means. Protocols for using these buffers and reagents for performing different steps of the procedure may be included in the kit.

The reagents may be supplied in a solid (e.g., lyophilized) or liquid form. The kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

In certain aspects, the kits of the present invention further include control samples. In other aspects of the invention, the inventive kits include at least one expression profile map for a GVHD, IPS and/or IPS sub-type as described herein for use as comparison template. Preferably, the expression profile map is digital information stored in a computer-readable medium.

Instructions for using the kit, according to one or more methods of the invention, may comprise instructions for processing the biological sample obtained from the subject, and/or for performing the test, instructions for interpreting the results. As well as a notice in the form prescribed by a governmental agency (e.g., FDA) regulating the manufacture, use or sale of pharmaceuticals or biological products.

EXAMPLE

Using label free expression proteomic and bioinformatic analyses, we have discovered and verified novel biomarkers of IPS progression after transplant. In particular, we identified markers that can subtype stem cell transplant patients who: 1) are likely to develop IPS, and 2) are likely to respond well to etanercept treatment. These markers can be used as prognostic tools to effectively target and trigger therapeutic intervention earlier than currently described. The following outlines the specific markers and assays in human plasma samples to detect these markers by mass spectrometry, ELISA, or related antibody and other methods.

Plasma EDTA was collected from IPS patients post blood marrow transplant and at the time of IPS diagnosis, while for the control (non-progressors group) samples were post-transplant and 14 days after transplant. Thus, there were two patient types; bone marrow transplant/– IPS and bone marrow transplant/+ IPS and two times of collection, post-BMT and approximately 2 weeks later. A total of 22 samples were depleted of the 7 most abundant proteins using standard methods. One hundred micrograms of each sample was digested with trypsin and a fraction of this digest (600 nanograms) was analyzed by LC/MS/MS via capillary liquid chromatography and a LTQ-FT. Automated differential quantification of peptides was accomplished using ProteoMarker. Peptide and protein identifications were integrated with these quantifications and used for statistical analysis via mixed multi-way ANOVA. 2025 peptides across 22 plasma samples were tracked in our analysis. Of these peptides, 1253 received a statistically significant sequence assignment and of those 552 peptides had p-values of <0.05 when analyzed by ANOVA (with adjustment for false discovery rates) for disease and time comparisons of cases versus controls. These peptides are derived from 102 distinct proteins and changes in their abundance in a patient are significant predictors of IPS progression. The 102 proteins identified along with their corresponding change in abundance (identified as + for increase in abundance and – for decrease in abundance) are listed in Table 5.

TABLE 5

| Desc | t |
|---|---|
| A1BG Alpha-1B-glycoprotein | −2.4717 |
| A2M Alpha-2-macroglobulin | −1.92582 |
| AFM Afamin | −3.74093 |
| AGT Angiotensinogen | 4.317323 |

TABLE 5-continued

| Desc | t |
|---|---|
| AHSG Alpha-2-HS-glycoprotein | −4.69926 |
| ALDOB Fructose-bisphosphate aldolase B | −2.0052 |
| AMBP AMBP protein | 0.341469 |
| APCS Serum amyloid P-component | 2.578971 |
| APOA1 Apolipoprotein A-I | −3.44706 |
| APOA2 Apolipoprotein A-II | −3.44494 |
| APOA4 Apolipoprotein A-IV | 0.140954 |
| APOA4 apolipoprotein A-IV precursor | −2.11612 |
| APOB Apolipoprotein B-100 | 1.123166 |
| APOC3 Apolipoprotein C-III | 1.616698 |
| APOD Apolipoprotein D | −2.462 |
| APOE Apolipoprotein E | 3.272737 |
| APOF apolipoprotein F precursor | −2.17694 |
| APOH Beta-2-glycoprotein 1 | −2.92375 |
| APOL1 Isoform 2 of Apolipoprotein-L1 | −1.59928 |
| APOM Apolipoprotein M | −4.99022 |
| ATRN Isoform 3 of Attractin | −2.13266 |
| AZGP1 alpha-2-glycoprotein 1, zinc | 2.018238 |
| BTD biotinidase precursor | −2.56362 |
| C14orf39 Protein SIX6OS1 | 3.640615 |
| C1QB complement component 1, q subcomponent, B chain precursor | −1.97171 |
| C1QC Complement C1q subcomponent subunit C | 3.220511 |
| C1R Complement C1r subcomponent | −0.65396 |
| C1RL Complement C1r subcomponent-like protein | −2.2814 |
| C1S Uncharacterized Protein | 0.860878 |
| C3 Complement C3 (Fragment) | −1.30768 |
| C4A Complement component 4A | −1.97228 |
| C4B complement component 4B preproprotein | 1.571717 |
| C4BPA C4b-binding protein alpha chain | 0.878785 |
| C4BPB Isoform 2 of C4b-binding protein beta chain | −2.42133 |
| C5 Complement C5 | −1.35444 |
| C6 Complement Component Precursor | −2.25676 |
| C7 Complement component C7 | −2.01065 |
| C8A Complement component C8 alpha chain | −2.1207 |
| C8B Complement component C8 beta chain | −2.0818 |
| C8G Complement component C8 gamma chain | −1.95742 |
| C9 Complement component C9 | 2.086113 |
| Carboxypeptidase N subunit | −2.32317 |
| CFB Isoform 1 of Complement factor B (Fragment) | 1.979763 |
| CFH Isoform 1 of Complement factor H | −1.36525 |
| CFHR2 Isoform Short of Complement factor H-related protein 2 | −2.1821 |
| CFI Complement factor I | −2.00425 |
| CLEC3B Putative uncharacterized protein DKFZp686H17246 | −2.19537 |
| CP Ceruloplasmin | 1.829568 |
| CPB2 Isoform 1 of Carboxypeptidase B2 | −2.25166 |
| CPN1 Carboxypeptidase N catalytic chain | −2.19879 |
| CRP Isoform 1 of C-reactive protein | 5.245925 |
| F12 Coagulation Factor | −2.18843 |
| F2 Prothrombin (Fragment) | −1.39156 |
| FCN3 Isoform 1 of Ficolin-3 | 1.856238 |
| FGA Isoform 2 of Fibrinogen alpha chain | 0.612848 |
| GC vitamin D-binding protein precursor | −2.1762 |
| GMPR2 GMPR2 protein | 2.702804 |
| GPX3 Glutathione peroxidase 3 | 2.028996 |
| GSN Isoform 1 of Gelsolin | −2.64335 |
| HBB Hemoglobin subunit beta | −2.12803 |
| HPX Hemopexin | −2.95159 |
| HRG Histidine-rich glycoprotein | −3.49181 |
| IGFALS Insulin-like growth factor-binding protein complex acid labile chain | −2.15608 |
| ITIH1 Inter-alpha-trypsin inhibitor heavy chain H1 | −3.19335 |
| ITIH2 Inter-alpha-trypsin inhibitor heavy chain H2 | −3.99365 |
| ITIH3 Isoform 1 of Inter-alpha-trypsin inhibitor heavy chain H3 | −0.08417 |
| KLKB1 Plasma Kallikrein Precursor | −1.77692 |
| KNG1 Isoform LMW of Kininogen-1 | 0.824532 |
| KRT1 Keratin, type II cytoskeletal 1 | 2.690668 |
| LBP Lipopolysaccharide-binding protein | 3.048725 |
| LOC653879 similar to complement component 3 | −2.10055 |
| LRG1 Leucine-rich alpha-2-glycoprotein | 3.361271 |
| LUM Lumican | −2.23514 |
| MBL2 Mannose-binding protein C | −1.97585 |
| ORM1 Alpha-1-acid glycoprotein 1 | 3.804263 |
| ORM2 Alpha-1-acid glycoprotein 2 | 2.96858 |
| PGLYRP2 Isoform 1 of N-acetylmuramoyl-L-alanine | −2.68326 |

TABLE 5-continued

| Desc | t |
| --- | --- |
| amidase | |
| PLG Plasminogen | −2.23116 |
| PON1 Serum paraoxonase/arylesterase 1 | −2.03837 |
| PON3 Serum paraoxonase/lactonase 3 | −1.90156 |
| PROS1 Vitamin K-dependent protein S | −2.28215 |
| RBP4 Retinol binding protein 4, plasma | −0.03233 |
| S100A9 Protein S100-A9 | −2.76747 |
| SAA1; SAA2 Serum amyloid A protein | 2.706316 |
| SAA1; SAA2 serum amyloid A2 isoform a | 5.079694 |
| SAA4 Serum amyloid A-4 protein | −1.70284 |
| SERPINA1 Isoform 1 of Alpha-1-antitrypsin | 2.025056 |
| SERPINA3 Isoform 1 of Alpha-1-antichymotrypsin | 3.737104 |
| SERPINA4 Kallistatin | −1.94552 |
| SERPINA6 Corticosteroid-binding globulin | −2.90036 |
| SERPINA7 Thyroxine-binding globulin | −1.76982 |
| SERPIND1 Serpin peptidase inhibitor, clade D (Heparin cofactor), member 1 | −0.9005 |
| SERPINF1 Pigment epithelium-derived factor | 0.644739 |
| SERPINF2 SERPINF2 protein | −0.96973 |
| SERPING1 Plasma protease C1 inhibitor | 1.318974 |
| SHBG Isoform 1 of Sex hormone-binding globulin | −2.19629 |
| SLC26A6 Anchor protein | 2.696059 |
| SLC27A6 Long-chain fatty acid transport protein 6 | −1.78318 |
| TCP11L1 cDNA FLJ11386 fis, clone HEMBA1000523, weakly similar to TESTIS-SPECIFIC PROTEIN PBS13 | −1.80354 |
| TTR Transthyretin | −1.76341 |
| UBTF Isoform UBF2 of Nucleolar transcription factor 1 | −3.74554 |
| VTN Vitronectin | −3.16218 |

Table 5 represents 102 distinct proteins that were identified from the significant peptides. These represent proteins for which antibody assays can be developed for clinical detection. These data was subsequently incorporated with existing molecular networks and disease specific literature via Pathway Studio, IPA software packages and additional tools for an extended biological analysis. Moreover, many proteins identified as significant in the label free analysis are consistent with studies conducted on animal models of IPS. One example is lipid polysaccharide binding protein (LBP). This protein is involved in the acute-phase immunologic response to gram-negative bacterial infections by binding to endogenous endotoxin (LPS), which is a potent enhancer of inflammatory cytokine release. LPS levels rise in mice with IPS and studies in experimental models suggest that LPS elicits a severe, acute inflammatory response in the lungs (Cooke et al., *Blood* (1996) 88(8); 3230-3239; Nelson et al., *J. Infect Dis* (1989) 159(2); 189-194; Smith et al., *Am J Respir Cell Mol Biol* (1998) 19(6):881-891.) In addition, proteins responsible for regulation of the immune response such as lumican and attractin (Carlson et al., *J Biol Chem* (2005) 280(27):25541-25547; Duke-Cohan et al., *Proc Natl Acad Sci USA* (1998) 95(19):11336-11341; Johnson et al., *Invest Ophthalmol Vis Sci* (2005) 46(2):589-595; Wrenger et al., *J Leukoc boil* (2006) 80(3):621-629), which were previously not associated with this disease were identified as significant in the label free expression study. Lumican is of particular interest as it has been suggested that lumican regulates antigen sensing by Toll-like receptors 4 and innate immune response.

To probe the potential for lumican abundance levels to be used as a potential early indicator for progression to IPS, we examined the individual expression values for this protein in individual patients. This analysis has detected increased lumican levels prior to clinical diagnosis of this complication (day 0), the levels are most strikingly elevated for the IPS patients that responded well to the specific treatment strategy with etanercept. It is clear that therapy with etanercept can be guided by a molecular diagnostic in plasma for lumican, where bone-marrow transplant patients with elevated lumican levels would be treated immediately, with likely beneficial effects that might entirely suppress development of IPS.

In addition, a disease specific molecular network was generated via incorporation of statistically significant proteins, existing molecular networks and disease specific literature. The data demonstrated that attributes of the innate immune system contribute to the patho-physiology of IPS in SCT patients and many proteins identified as significant in the label free analysis are consistent with studies conducted on animal models of this disease such as lipid polysaccharide binding protein (LBP). In addition, proteins responsible for regulation of the immune response which were previously not associated with this disease were identified as significant in the label free expression study. Finally, the observed increases of LBP in patients with IPS have been verified via ELISA techniques.

Experimental Procedures

Patients and Patient Controls

Patients were recruited from May 2001 to February 2004 at the Blood and Marrow Transplantation Programs in the University of Michigan Medical Center and the Dana Faber Cancer Institute and were required to be at least 1 year of age, were within 100 days of receiving an allogeneic SCT and had IPS as defined by the NIH working group criteria. Patients were excluded from this study after the time of enrollment if they: 1) had a positive culture of bronchoalvelor lavage fluid (BAL) for active pulmonary infection; 2) had hypotension in which inotropic support other than dopamine at less than 5 μg/kg per minute was required; 3) had bacteremia within 48 hours before the entry into the study; 4) were positive for cytomegalovirus viremia via CMV polymerase chain reaction or pp 65 antigenemia tests; 5) had systemic fungal or other non bacterial infections; or 6) had clinical evidence for cardiac dysfunction as the cause of respiratory failure. Controls were from SCT patients who had no complications from transplantation through day 10.

Diagnostic Procedures

Chest radiography, bronchoscopy with BAL, CMV blood assay, aerobic blood cultures and clinical assessment of pulmonary dysfunction was performed on all patients at the time of study entry. Pulmonary function was determined via blood gas measurements and chest radiographs were performed twice with the first 7 days of treatment and then weekly through day 28. CMV assays were performed weekly through day 28.

Plasma Samples

Blood was obtained for label free expression at the time of bone marrow transplant and at either the time of IPS diagnosis for patients or obtained between 14 and 21 days after transplant for patient controls. Blood was collected in heparinzed tubes and plasma was separated and stored at −80° C. until analysis.

Experimental Design for Label Free Analysis

The categorical factors under study consist of a Disease Factor (DF) crossed with a Time factor (TF) for which their main effects and possible interaction are of interest. The two levels of the Disease factor were the two groups of patients who both received the bone marrow transplant (SCT) and who were further either diagnosed with IPS (Progressors—P) or underwent no complications (Controls—C). The two levels of the time factor were the two time-points on the day of BMT (Day-0) and on the day of IPS diagnosis for both controls and patient (Day-X for Progressors and Day-14 for Controls). These later two days (Day-X or Day-14) were further assumed to be the same in the statistical analysis. The experimental units under study are the patients (sample size:

n=11), assumed to be independent and randomly sampled from the entire population meeting inclusion criteria. The Disease factor represents the variable over which repeated measures were made within each experimental unit.

Further, each combination of Disease×Time treatment was randomized (without blocking) among 5 and 6 experimental units (biological replicates) of Progressors and Controls respectively. Therefore, this is a Factorial Arrangement of treatments (Disease×Time) laid out on an unbalanced Completely Randomized Design (CRD) with repeated measures on one treatment (Disease).

Sample Preparation

Individual plasma samples were depleted of the seven most abundant proteins using a 4.6×100 mm multiple affinity removal system (MARS Hu7, Agilent Technologies, Santa Clara, Calif.) according to manufacturer's instructions. Each depleted sample was concentrated (5,000 molecular weight cutoff, Millipore, Billerica, Mass.) and buffer exchanged with 50 mM Tris to a final volume of approximately 100 microliters. Total protein concentrations were determined by 2D Quant Kit as described by the manufacturer (GE Healthcare Piscataway, N.J.) and 10 micorgrams of flow through and bound fractions for each sample were loaded onto a one dimensional SDS-PAGE gel (4-20% Tris-HCL) as a quality control measure for the depletion step. Subsequent to digestion, each sample was adjusted to 60 micrograms in 50 µL. Twenty microliters of 0.2% Rapigest (Waters, Milford, Mass.) and dithiotheritol to a final concentration of 5 mM was added. The samples were reduced at 80° C. for 15 minutes and cooled to room temperature prior to alkylation with iodacetamide at a final concentration of 10 mM for 30 minutes. Proteolytic digestion was performed with bovine trypsin (Promega, Madison, Wis.) with a final enzyme to protein ration 1:10 (w/w) of for 18 hours at 37° C.

Label Free Expression

Liquid Chromatography and Mass Spectrometry

Three hundred nanograms of each sample were analyzed by LC/MS/MS and the order of sample injections randomized over all samples. Separation of peptides via capillary liquid chromatography was performed using a Dionex Ultimate 3000 capillary LC system (Dionex Sunnyvale, Calif.). Mobile phase A (aqueous) contains 0.1% formic acid in 5% acetonitrile and mobile phase B (organic) contained 0.1% formic acid in 85% acetonitrile. Samples were trapped and desalted on-line in mobile phase A at 10 µL/min for 10 minutes using a Dionex PepMap 100, (300 µm×5 mm) The sample was subsequently loaded onto a Dionex C18 PepMap (75 µm×15 cm) reversed phase column with 5% mobile phase B. Separation was obtained by employing a gradient of 6% to 28% mobile B at 0.300 µL/min over 100 minutes. The column was washed at 99% mobile phase B for 10 minutes, followed by a re-equilibration at 100% A for 17 minutes. Mass spectrometry analyses of samples were performed using a hybrid linear ion trap Fourier-transformation cyclotron resonance mass spectrometer (LTQ-FT, Thermo, Waltham, Mass.). Positive mode electrospray was conducted using a nanospray source and the mass spectrometer was operated at a resolution of 25,000. Quantitative and qualitative data were acquired using alternating full MS scan and MS/MS scans in normal mode. Survey data were acquired from m/z of 400 to 1600 and up to 3 precursors based on intensity, were interrogated by MS/MS per switch. Two micro scans were acquired for every precursor interrogated and MS/MS was acquired as centroid data. The FT and LTQ were mass calibrated immediately before the analysis using the instrument protocol. Raw LC/MS/MS data was processed via Proteomarker software (Infochromics, Toronto, Canada).

Data Processing—Qualitative and Quantitative

The raw data were for each run were first extracted to provide MS/MS peak lists for identification and intensity based profile peak lists for quantification. The MS/MS peak lists were subsequently searched by Mascot version 2.2.0 (Matrix Science London, UK). The database used was the human International Protein Index (IPI) (68020 sequences). Search settings were as follows: trypsin enzyme specificity, mass accuracy window for precursor ion, 10 ppm; mass accuracy window for fragment ions, 0.8 Daltons; variable modification, including only carbamidomethylation of cysteines and oxidation of methionine. The criteria for peptide identification were a mass accuracy of <10 ppm and an expectation value of $p \leq 0.05$. Proteins that had >2 peptides matching the above criteria were considered confirmed assignments while proteins identified with one peptide regardless of the Mascot score were highlighted as tentative assignments.

Network Analysis of Label Free Expression Data

Following statistical analysis, significant proteins with their corresponding abundance change were imported into Ingenuity Pathway Analysis (Ingenuity Systems, Redwood City, Calif., USA). This software utilizes biomedical literature and existing protein interaction databases to elucidate biological networks within uploaded protein lists (Ingenuity®, www.ingenuity.com). This is accomplished by estimates of significance and ranking of biological networks and pathways identified via the right tailed distribution of Fisher's exact test. In addition, we have controlled the false discovery rate (FDR) by setting a threshold in the software of q-values of 0.1, which means that no more than 10% of all pathways identified as significant are false positives.

Results

Label Free Expression Analysis

The sample depletion protocol was reproducible across individual samples and yielded sufficient protein concentrations for the bound fraction with ranges of 1.7 µg/µL to 5.4 µg/µL. Reproducible protein patterns via 1D-SDS PAGE were observed across all samples for both flow-through and bound fractions (data not shown). These depleted samples were subsequently digested and analyzed by LC/MS/MS as described in the methods section. The optimized LC/MS/MS analysis provided excellent chromatographic reproducibility across experimental groups and injections.

Network Analysis of Significantly Changing Proteins

Proteins that were identified as significant in the above statistical analysis were subsequently imported into IPA for network analysis and two immune related networks were identified. FIG. 6 highlights the biological functions associated with these networks and their statistical significance. Interestingly, the top functions identified were immune related and were highly significant as 43 of the 79 proteins imported into IPA were associated with immune related processes. One canonical pathway which was identified as significant was acute phase response signaling which was anticipated as IPS elicits a severe inflammatory response in patients.

Biological Significance of Networks Identified

Footprints of TNF-α and IL-6 Signaling

The acute phase response (APR) is an innate systemic immune response to injury and/or infection. It involves the altered expression of proteins synthesized in the liver whose plasma concentrations increase (positive acute phase reactants) or decrease (negative acute phase reactants) in response to circulating inflammatory cytokines such IL-6, IL-1 and TNF-α. Due to this relationship, these serum proteins can serve as "readouts" of the Acute Phase Signaling Response (APSR) and the key cytokines involved in its regulation.

Good correlation was observed for both negative and positive acute phase reactants with respect to their abundance change in plasma. Six of the eight negative acute phase reactants identified as significant in the interaction effect were observed to decrease in abundance while 16 of 28 positive acute phase reactants plasma abundances increased. This data provides additional evidence and cross validation of cytokine up-regulation in IPS patients as previous ELISA assays for TNF-α and IL-6 have shown significant increases in protein concentrations in both BAL fluid and plasma of IPS patients when compared to allogeneic HCT patients without IPS.

Activation of the Innate Immune Response

The innate immune response is primarily mediated by antigen presenting cells (APCs) and phagocytic cells both of which require activation via pattern recognition of evolutionary conserved structures on pathogens. These structures are also known as pathogen-associated molecular patterns (PAMPs) and are detected via pattern recognition molecules such as Toll like receptors (TLRs) and LPS binding protein (LBP). Once detected, their engagement with TLRs on the cell surface triggers a cascade of signaling events, which culminate in the production of proinflammatory cytokines. LBP is a well characterized acute phase protein which binds endotoxin. TLR4 activation and sensitivity to endotoxin relies on a series of interactions starting with LBP that enables optimal presentation of endotoxin to TLR4. In addition to bacterial recognition, LBP also can indirectly regulate the inflammatory response. Numerous studies in LBP knockout mice have shown that the absence of LBP leads to reduce LPS responsiveness and immune activation. In addition, recent work have found acute phase LBP levels block TLR4 signally and subsequent TNF-α secretion suggesting an inhibitory role for LBP at very high concentrations. In our study, average LBP levels were slightly higher in IPS patients at day 0 than controls and a significant increase in IPS patients was observed at diagnosis when compared to controls. Moreover, this increase was observed in both the label free experiment as well as an ELISA detecting LBP on a larger subset from this cohort providing cross validation of the analytical platforms.

As mentioned above, aside from LBP a number of other pattern recognition molecules were identified as significant from our analysis. Mannose binding protein C (MBL), peptidoglycan recognition protein 2 and lumican are also pattern recognition proteins and had similar interaction profiles with increases in abundance in IPS patients at day 0 when compared to controls at the same timepoint. MBL is a serum protein, which is synthesized in the liver. It belongs to the collectin protein family that consists of collagenous and lectin domains. In addition, it contains a carbohydrate recognition domain, which enables it to bind polysaccharide structures presented by pathogens and activates complement via the lectin pathway. Traditionally, its role in the innate immune response and inflammation was thought to be attributed to its ability to trigger the lectin pathway but recent studies have demonstrated an ability to modulate the inflammatory response. The proposed mechanism by which this modulation occurs is via MBL acting as a TLR2/TLR6 co-receptor within the cell. In vitro studies have shown that MBL binds to LTA and complexes with TLR 2 within the phagosome increasing efficiency of ligand delivery within the macrophage and subsequent cytokine signaling. In our analysis, a single peptide was identified for MBL, therefore, it is not included in our confirmed protein list. However, the MBL peptide had a very high mascot score (score=95) which corresponded to a $1.0e^{-009}$ probability of a correct assignment and was also significant for the interaction effect.

Whereas LBP and MBL have defined biological functions and well established roles in the innate immune response, PGLYRP2 and lumican have recently been identified as pattern recognition proteins. Peptidoglycan recognition proteins (PGRPs) are innate immunity proteins that contain a well conserved peptidoglycan binding type 2 amidase domain across most animals. In mammals, PGLYRP2 is a member of a family of peptidoglycan recognition proteins that also includes PGLYRP1, 3 and 4. Mammalian PGLYRP2 is a serum protein produced by the liver which has peptidoglycan amidase acitivity and whose role in the immune response was proposed as an anti-inflammatory scavenger of peptidoglycan. However, recent studies in a peptidoglycan induced arthritis animal model have demonstrated that PGLYRP2 has pro-inflammatory properties. In this work, PGLYRP2 was found to locally modulate the inflammatory response via cooperation with other pattern recognition molecules specifically Nod2 and TLR4 both of which are important regulators of signaling cascades involved in the production of pro-inflammatory cytokines. Five peptides of PGLYRP2 were identified in the label free analysis as significant for the interaction effect. The interaction profile was similar to MBL with higher levels observed at day 0 for IPS than controls at the same time point (FIG. 1).

Figure 2:
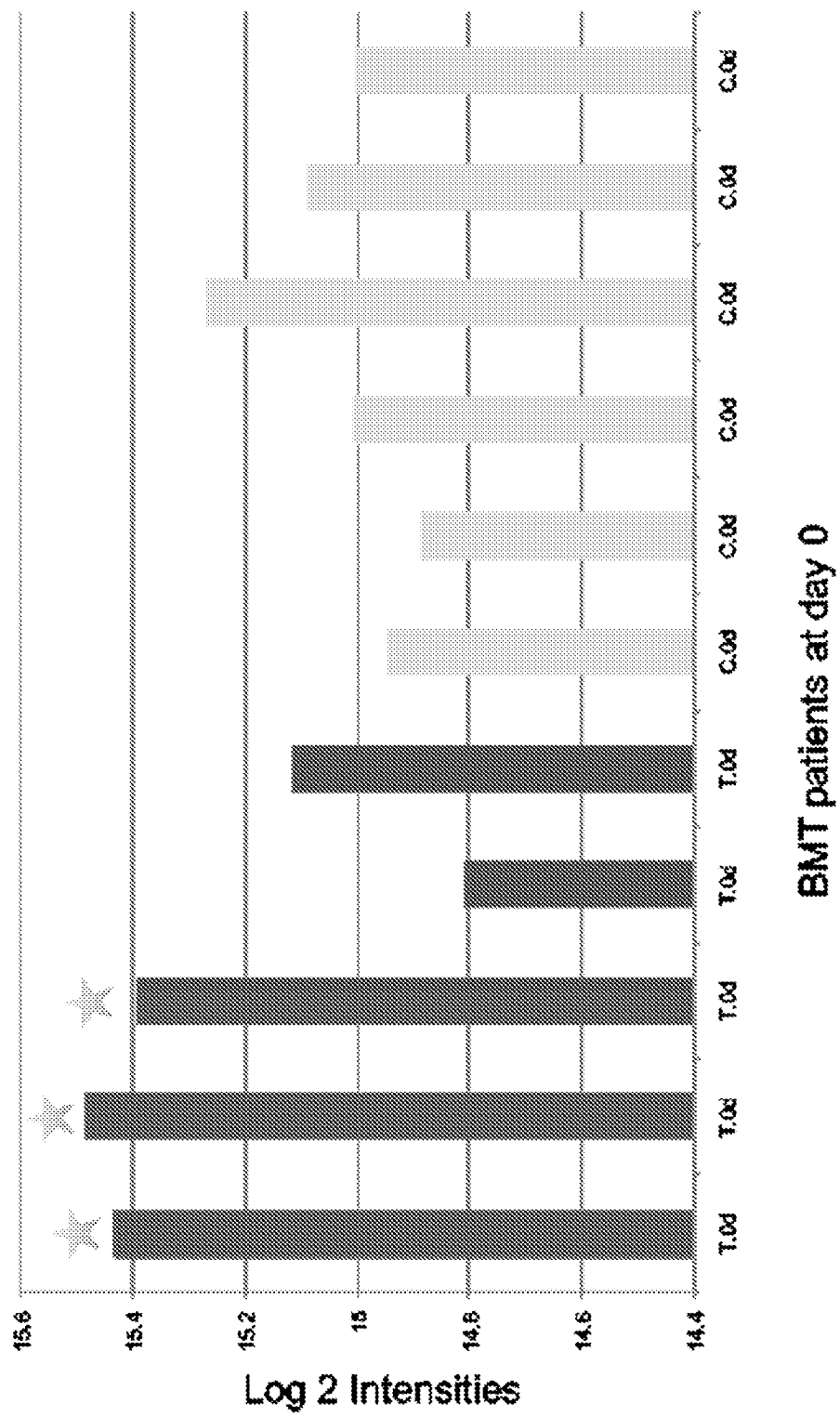
FIG. 2 is a graphical illustration of the distribution of average lumican peptide intensity (non-log scale) across individual subjects at day 0 for control (C) and IPS (T) in accordance with an example of the present invention. Subjects highlight with a star denote IPS subjects who responded to treatment.

As mentioned above, lumican is another protein identified in our analysis that has recently been shown to be involved in the innate immune response and pattern recognition. Lumican is a small leucine rich glycoprotein which is expressed is a variety of tissues and is extracellular matrix protein. A study which utilized a lumican knock out model to investigate the role of lumican in wound healing found $Lum^{-/-}$ mice had poor recruitment of macrophages to the site of injury as well as a significant decrease in the induction of inflammatory cytokines. Moreover, additional knock out studies have found functional impairment of the innate immune inflammatory response. In this work, $Lum^{-/-}$ mice challenged with LPS were resistant to septic shock and death with poor induction of TNF-α and IL-6. Moreover this study found lumican expression is induced during the innate immune response, LPS binds to lumican and co-precipitates with CD14 which is a key regulator of LPS sensing. Taken together, this data suggest lumican may have an important role in mediating antigen sensing and may enhance host sensitivity to LPS. In the label free analysis, four peptides for lumican were identified as significant for the interaction effect. Three of the five IPS patients had higher levels at day 0 for IPS than controls at the same time point. FIG. 2 highlights the distribution of average peptide intensity for this protein. A 40% increase in average peptide abundance (non log scale) was observed for these three subjects when compared to other subjects analyzed in this study. Interestingly, these three IPS subjects responded to etanercept therapy with greater than a 100 day survival after treatment.

Figure 3:
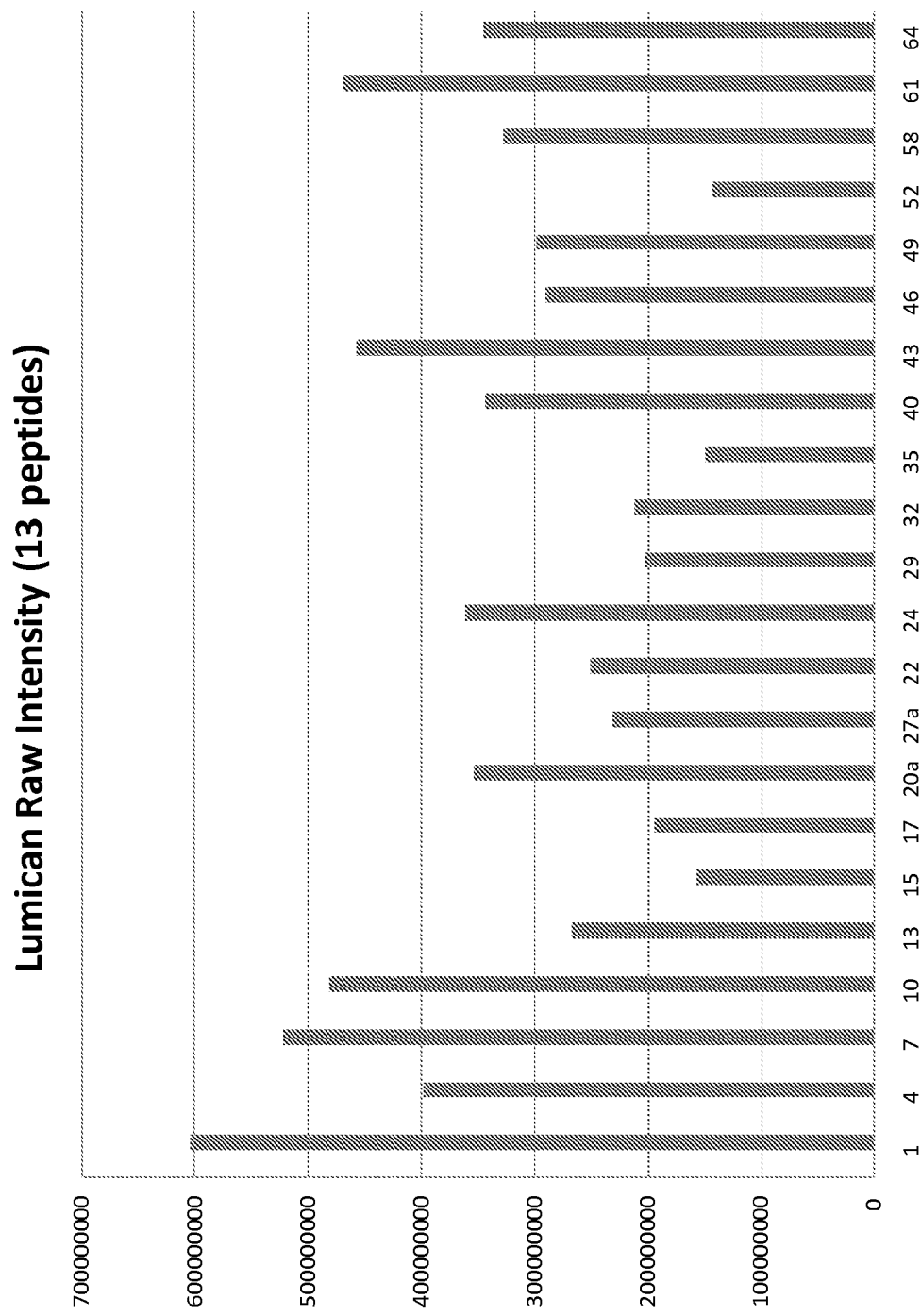
FIG. 3 is a graphical illustration of average lumican peptide intensity (non-log scale) across individual subjects at day 0 in accordance with another example of the present invention.

FIG. 3 highlights the distribution of average peptide intensity for lumican for 21 of the 22 patients. The data for patient number 46 (i.e., the $22^{nd}$ patient) was omitted because of substantially elevated cytokine levels were detected in this patient by ELISA. Lumican levels were found to be down about 8% in progressors vs. non-proegrssors (day 0 post transplantation compared to day 14 post transplantation) and up 188% for responders vs. non responders to therapy (day 0 post transplantation).

Figure 4:
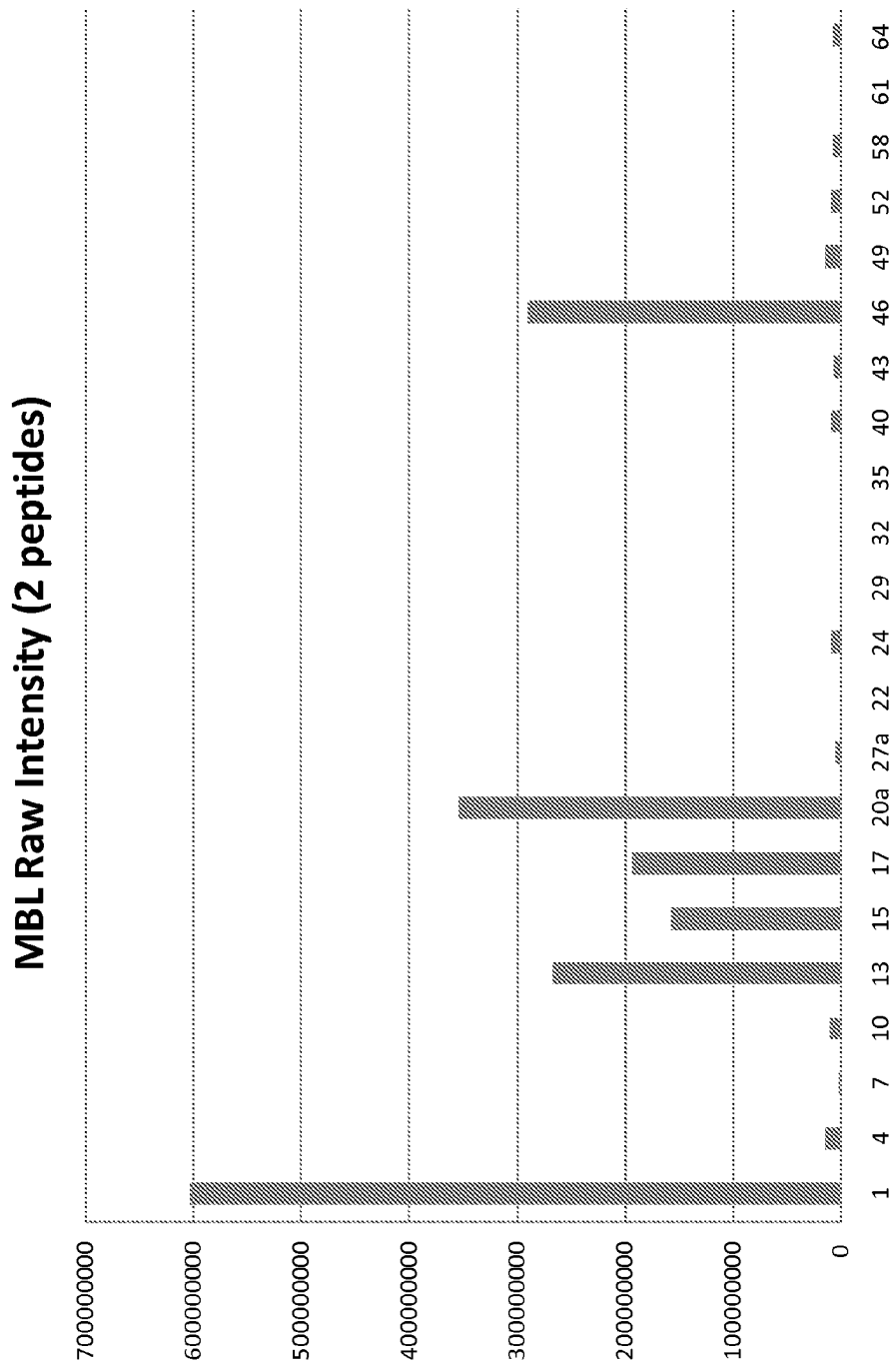
FIG. 4 is a graphical illustration of average Mannose-binding protein C (MBL2) intensity (non-log scale) across individual subjects at day 0 in accordance with another example of the present invention.

FIG. 4 highlights the distribution of average peptide intensity for MBL2 Mannose-binding protein C for 21 of the 22 patients. MBL2 Mannose-binding protein C levels were found to be up 1345% in progressors vs. non progressors (day 0 post transplantation compared to day 14 post transplantation) and up 58% in responders vs. non responders (day 0 post transplantation).

Figure 5:
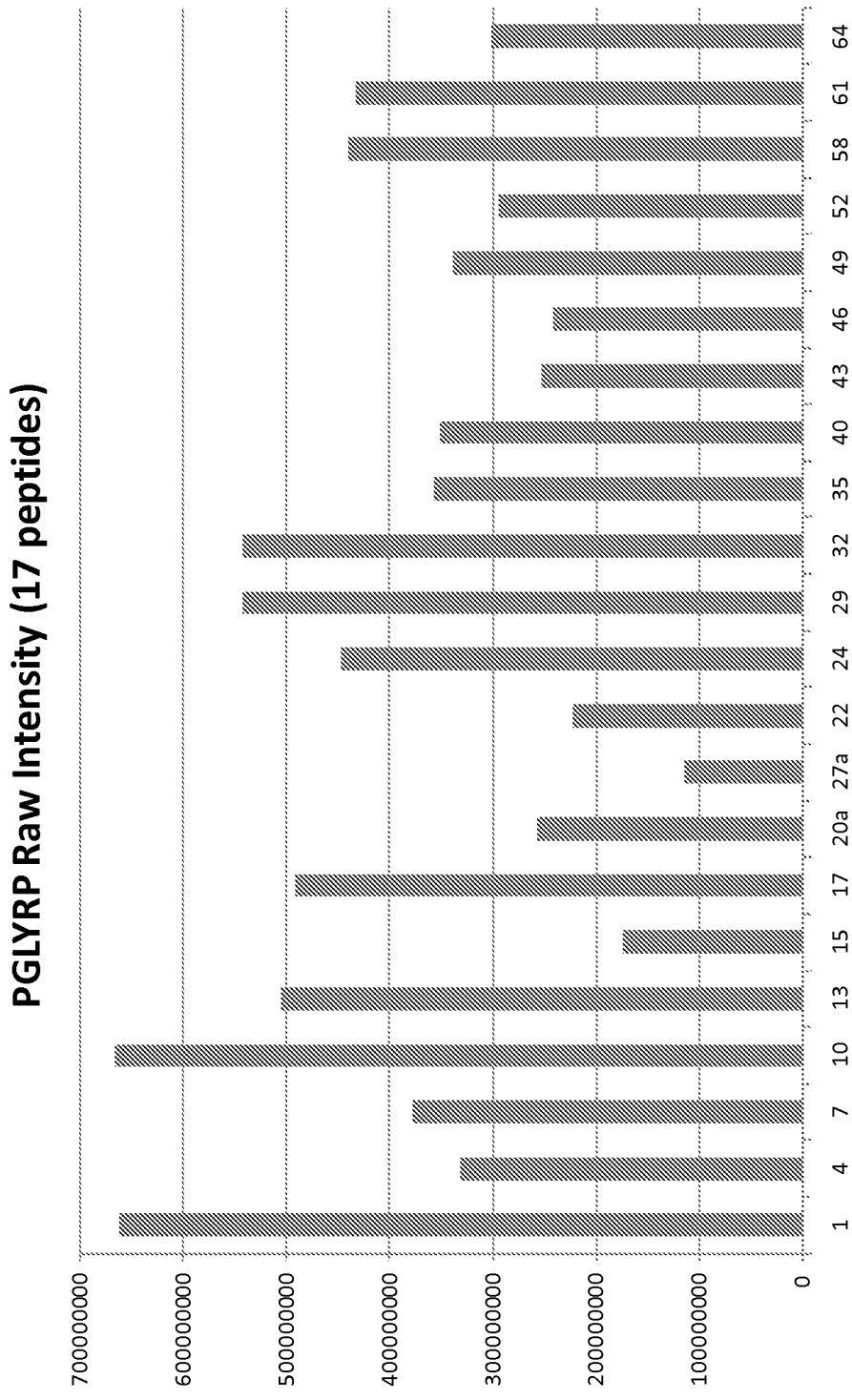
FIG. 5 is a graphical illustration of average peptidoglycan recognition protein (PGLYRP2) (non-log scale) across individual subjects at day 0 in accordance with another example of the present invention.

FIG. 5 highlights the distribution of average peptide intensity for PGLYRP peptidoglycan recognition protein for 21 of the 22 patients. PGLYRP peptidoglycan recognition protein levels were found to be up 189% in progressors vs. non progressors (day 0 post transplantation compared to day 14 post transplantation) and up 88% in responders vs. non responders (day 0 post transplantation).

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, the following is claimed:

1. A method for identifying idiopathic pneumonia syndrome (IPS) progression in a subject following allogeneic hematopoietic stem cell transplantation, the method comprising:

obtaining a biological sample from the subject, wherein the biological sample comprises a sample of blood, plasma, serum, or bronchoalveolar lavage fluid, wherein the subject has received the allogeneic hematopoietic stem cell transplantation; and determining in the biological sample a level of Mannose-binding protein C;

comparing the measured level of Mannose-binding protein C to a control level prior to transplantation; and identifying the IPS as progressing if the level of Mannose-binding protein C determined is decreased at least about 5% compared to the control level.

2. The method of claim 1, wherein a decrease of at least about 20% in the determined level of Mannose-binding protein C compared to the control level characterizes the IPS in the subject as progressing.

3. The method of claim 1, wherein the IPS is a subtype of idiopathic pneumonia syndrome that is responsive to treatment by a TNF-$\alpha$ inhibitor, wherein the TNF-$\alpha$ inhibitor is selected from the group consisting of etanercept, infliximab, adalimumab, certolizumab pegol, gohmumab (simponi), lenercept, semapimod, pentoxifylline, thalidomide, and benzopyranes.

* * * * *